(12) United States Patent
Kanter et al.

(10) Patent No.: US 8,252,775 B2
(45) Date of Patent: Aug. 28, 2012

(54) METHOD OF TREATING MULTIPLE SCLEROSIS WITH PHOSPHOCHOLINE CONTAINING LIPIDS

(75) Inventors: Jennifer L. Kanter, Boston, MA (US); William H. Robinson, Palo Alto, CA (US); Lawrence Steinman, Stanford, CA (US)

(73) Assignees: The Board of Trustees of the Leland Stanford Junior University, Palo Alto, CA (US); U.S. Department of Veteran Affairs, Washington, DC (US)

( * ) Notice: Subject to any disclaimer, the term of this patent is extended or adjusted under 35 U.S.C. 154(b) by 1359 days.

(21) Appl. No.: 11/491,409

(22) Filed: Jul. 21, 2006

(65) Prior Publication Data

US 2007/0020691 A1    Jan. 25, 2007

Related U.S. Application Data

(60) Provisional application No. 60/701,662, filed on Jul. 21, 2005.

(51) Int. Cl.
*A01N 57/10* (2006.01)
*A61K 31/66* (2006.01)

(52) U.S. Cl. ....................... 514/109; 514/114
(58) Field of Classification Search .................... 514/183
See application file for complete search history.

(56) References Cited

U.S. PATENT DOCUMENTS

| | | | |
|---|---|---|---|
| 5,976,543 A * | 11/1999 | Ben-Nun | 424/190.1 |
| 2002/0187509 A1 | 12/2002 | Shao et al. | |
| 2003/0003516 A1 * | 1/2003 | Robinson et al. | 435/7.9 |
| 2003/0171277 A1 * | 9/2003 | Fogelman et al. | 514/12 |
| 2004/0185445 A1 | 9/2004 | Fang | |
| 2006/0173067 A1 * | 8/2006 | Fogelman et al. | 514/423 |
| 2009/0036410 A1 * | 2/2009 | Harbige et al. | 514/114 |

OTHER PUBLICATIONS

Kanter, Development of Lipid Microarrays for identification of autoantibodies to myelin and subsequent countermeasures for therapy of multiple sclerosis, Jun. 2006, Diss. Abstr. Int., Stanford University, cover pages, abstract, pp. 2-8, 24-26, 33-34, 49-57 and 78-83.*
Groves et al., "Substrate-Membrane Interactions: Mechanisms for Imposing Patterns on a Fluid Bilayer Membrane," Langmuir, 1998, 14(12):3347-3350.
Hovis et al., "Patterning Barriers to Lateral Diffusion in Supported Lipid Bilayer Membranes by Blotting and Stamping," Langmuir, 2000, 16(3):894-897.
Kidd, "Multiple sclerosis, an autoimmune inflammatory disease: prospects for its integrative management," Altern. Med. Rev., 2001, 6(6):540-566.
Battistini, L., et al., "CD1b is expressed in multiple sclerosis lesions," (1996) *Journal of Neurobiology*, 67:145-151.
Fang, Y., et al., "Ganglioside microarrays for toxin detection," (2003) *Langmuir*, 19:1500-1505.
Forrester, J.S., et al., "Computational lipidomics: a multiplexed analysis of dynamic changes in membrane lipid composition during signal transduction," (2003) *Molecular Pharmacology*, 65(4):813-821.
Fredman, P., "The role of antiglycolipid antibodies in neurological disorders," (1998) *Annals New York Academy of Sciences*, 845:341-352.
Giovannoni, G., et al "Circulating antiganglioside antibodies are not associated with the development of progressive disease or cerebral atrophy in patients with multiple sclerosis," (2000) *Annals of Neurology*, 47(5):684-685.
Groves, J.T., et al., "Micropatterning fluid lipid bilayers on solid supports," (1997) *Science* 275:651-653.
Ivanova, P.T., et al., "Lipid arrays: new tools in the understanding of membrane dynamics and lipid signaling," (2004) *Molecular Interventions*, 4(2):86-96.
Jahng, A., et al., "Prevention of autoimmunity by targeting a distinct, noninvariant CD1d-reactive T cell population reactive to sulfatide," (2004) *The Journal of Experimental Medicine*, 2005(7):947-957.
Kanter, J., et al., "Methods for diagnosis and treatment of human autoimmune diseases by multiplex determination of autoantibody specificities to lipids—part II," (2005) *Invention Disclosure*, Jun. 14, 2005.
Lahiri, J., et al., "Lipid microarrays," (2001) *Biomedical microdevices*, 3(2):157-164.
Milne, S.R., et al, "Multiplexed lipid arrays of anti-immunoglobulin m-induced changes in the glycerophospholipid composition of WEHI-231 cells," (2003) *AfCS Research Reports*, 1(11) 1-11.
Moody, D.B., et al., "Anatomy of CD1-lipid antigen complexes," (2005) *Nature Reviews/Immunology*, 5:387-399.

* cited by examiner

*Primary Examiner* — Jeffrey S. Lundgren
*Assistant Examiner* — Meghan Finn
(74) *Attorney, Agent, or Firm* — Bozicevic, Field & Francis LLP; Pamela J. Sherwood

(57) ABSTRACT

To perform large-scale multiplex analysis of lipid-specific binding, lipid microarrays were developed. Lipids identified as disease associated, or analogs there, can be tolerogenic to patients suffering from autoimmune disease. Lipid array analysis has revealed anti-lipid antibodies in patients with immune disorders, and may contribute to the pathogenesis of disease.

5 Claims, 9 Drawing Sheets

Sphingomyelin

PGPC (1-palmitoyl-2-glutaroyl-sn-glycero-3-phosphocholine)

METHOD OF TREATING MULTIPLE SCLEROSIS WITH PHOSPHOCHOLINE CONTAINING LIPIDS

GOVERNMENT RIGHTS

This invention was made with Government support under contracts AR002133, DK061934, HV028183, and GM007276 awarded by the National Institutes of Health. An NIH U19 Pilot Award and a Department of Veteran's Affairs Merit Award also supported the work. The Government has certain rights in this invention.

INTRODUCTION

Lipids are important targets of immune responses in a variety of microbial and autoimmune diseases: However, immune responses to lipids have been studied much less extensively than responses to proteins largely due to lack of enabling technologies. Existing methods to study immune responses against lipids are hindered by the large number of potential lipid antigens, the hydrophobicity of lipids, and the technical difficulty of detecting B and T cell responses directed against lipids.

Multiple sclerosis (MS) is presumed to be an autoimmune disease targeting the myelin sheath in the central nervous system (CNS). Although researchers have demonstrated both T cell and autoantibody reactivity to myelin proteins including myelin basic protein (MBP), proteolipid protein (PLP), and myelin oligodendrocyte glycoprotein (MOG), the breadth and specificity of autoimmune responses in MS remain incompletely characterized. Lipids compose over seventy percent of the myelin sheath, and we now demonstrate that lipids are major targets of the autoantibody response in MS. Autoimmune responses directed against phospholipids and gangliosides contribute to the pathogenesis in systemic lupus erythematosus and Guillain Barré syndrome, respectively (Fredman (1998) *Ann N Y Acad Sci* 845, 341-52). Despite reports of anti-myelin lipid responses in MS, the role of anti-lipid autoimmunity in MS remains controversial (Giovannoni et al. (2000) *Ann Neurol* 47, 684-5). Most lipids are presented to T cells bound to CD1 molecules (Moody et al. (2005) *Nat Rev Immunol* 5, 387-99) and CD1 expression is increased in CNS lesions in both MS and EAE (Battistini et al. (1996) *J Neuroimmunol* 67, 145-51 (1996)).

While nucleic acid and protein arrays have been widely used, the use of lipids in microarrays has been more difficult. For example, arrays with probes composed of gangliosides that are embedded in lipid membranes have been used to detect toxins in a sample (Fang et al. Langmuir, 2003, 19, 1500-1505; Fang, U.S. Patent Application 20040185445.) Arrays of membranes may be obtained by fabricating grids of titanium oxide on a glass substrate as titanium oxide resists the adsorption of lipids (Boxer et al (1997) Science 275:651-653; and Boxer et al. (1998) Langmuir 14:3347-3350). To make membrane arrays by printing membranes on unpatterned surfaces, it has been necessary to confine the membrane to the printed areas without lateral diffusion of the membrane molecules to the unprinted areas, for example using poly-dimethylsiloxane (PDMS) stamps "inked" with phosphatidylcholine (PC) (Hovis et al (2000) Langmuir 2000:16, 894-897). Simplified methods of generating lipid microarrays would provide for improved functionality and wider use. Methods for the rapid multiplex analysis of binding specificities for lipids are of great interest for a variety of clinical and laboratory applications. The present invention addresses this need. We further provides methods for detection of anti-lipid antibodies for the diagnosis of autoimmune disease, and the therapeutic administration of lipids to treat autoimmune disease.

SUMMARY OF THE INVENTION

Multiplex lipid arrays are provided. A set of lipids, where lipids can include glycolipids, phospholipids, triglycerides, lipid complexes, etc., are arrayed on a substantially planar, hydrophobic substrate, which array is then available for determination of ligand binding to the lipids. In some embodiments of the invention, the lipids are arrayed in a hydrophobic membrane, having a pore size of from about 0.05 to 5 µm, which is stable to organic solvents. Lipids of particular interest are biologically relevant, e.g. lipids present in cells and tissues of mammals, pathogens, plants, etc., which include, without limitation, lipid autoantigens. The arrays find use in a variety of applications. For example, an array can be used to test a blood, spinal fluid, or tissue sample for the presence of lipid-binding antibodies, or diagnose clinical pathology based upon presence of particular lipid-binding antibodies, or identify autoimmune patients likely to response to a lipid-based therapeutic. In another embodiment, a lipid array is used for the identification of lipids for use as therapeutics to treat autoimmune disease.

Methods of determining an antibody specificity profile in a patient with an immune-related disease may comprise: preparing a lipid antigen array comprising at least two lipids; physically contacting the lipid antigen array with a patient sample comprising antibodies; identifying the disease associated lipid antigens within the microarray, which bind to antibodies within the patient sample; comparing the antibodies bound to the disease associated lipid antigens with a control sample known to be associated with the disease and/or known to be free of the disease.

In one embodiment, profiling of lipid-specific autoantibodies is useful in diagnosis and prognosis of patients having an immune-related disease, which disease may include, without limitation, autoimmune diseases, particularly demyelinating autoimmune diseases. Diseases of interest include, without limitation, central nervous system and peripheral nervous system demyelinating diseases; systemic lupus erythematosus; and the scope of autoimmune disease may include atherosclerosis. Lipids useful in such profiling include, without limitation, a variety of glycolipids present in the myelin sheath. In some patients it is found that oxidized forms of lipids are particularly relevant to disease. Diagnostic purposes include establishing the diagnosis of an autoimmune disease, assessing the prognosis of patients with autoimmune disease, selecting patients for treatment with non-lipid (small molecule and recombinant protein therapeutics), and selecting patients for treatment with lipid therapeutics.

Methods of profiling lipid-specific autoantibodies include the array technology described herein, ELISA, RIA, etc. It is shown herein that the presence of lipid-specific autoantibodies distinguishes autoimmune diseases from other conditions. For example, Multiple Sclerosis is evidenced by the presence in patient samples, e.g. serum, CSF, etc. of antibodies specific for lipids, particularly lipids present in myelin, which may include sulfatide, sphingomyelin; oxidized lipids including 3β-hydroxy-5α-cholestan-15-one, and 1-palmitoyl-2-(9'-oxo-nonanoyl)-sn-glycero-3-phosphocholine (PGPC). Patents having progressive disease, e.g. primary progressive or secondary progressive, may have increased reactivity against ganglioside lipids, e.g. GM1, as compared to patients having relapsing remitting disease. Profiling of lipids thus provides a means of determining patient prognosis, and then utilizing appropriate treatment.

Anti-lipid specificity profiles are also useful for design and selection of specific therapies for immune-related diseases. In one embodiment, a high throughput determination is made of the spectrum of disease relevant lipid-specific antibodies present in patient serum by detailed binding analyses of these antibodies. The antibody specificity profile reveals the individual's complex immune response directed to one or more antigens having one or more epitopes. In one embodiment, antigen-specific therapies are selected based on the antibody-specificity profile. Individualized cocktails of antigen specific treatments can be formulated based on the patient's specificity profile. In another embodiment, identification of a consensus of common antibody specificity profiles between patients with the same immune disorder provides for formulation of a generic antigen-specific therapy to treat patients with that disease. The invention also provides a method for the identification of patients likely to develop a more severe form of disease, enabling selection of more aggressive therapy based on a patient's antibody specificity profile.

In another embodiment of the invention, methods are provided for tolerizing an individual to lipid autoantigens. It is shown that administration of a tolerizing dose of specific lipid molecules, which are optionally administered in conjunction with a tolerizing adjuvant, can prevent or decrease autoimmune responses, e.g. in the treatment or prevention of demyelinating autoimmune diseases; systemic lupus erythematosus, insulin dependent diabetes mellitus, etc.

In another embodiment, lipid therapeutics can be identified by screening candidate lipids for tolerizing activity by methods provided herein. Candidate therapeutic lipids are identified based on the presence of anti-lipid antibody reactivity in biological samples derived from patients with the autoimmune disease of interest. Disease protective (tolerizing or therapeutic) lipids are identified based on one or more assays, including testing the impact of the candidate lipids in mouse models of the autoimmune disease and on the function of autoreactive and other inflammatory cells. Lipids that provide efficacy in murine models of human autoimmune disease, inhibit activation and function of autoreactive lymphocytes and other inflammatory cells, and/or reduce production of pro-inflammatory cytokine and/or increase production of anti-inflammatory cytokines are likely to provide therapeutic benefit in human autoimmune and inflammatory diseases.

DETAILED DESCRIPTION OF THE EMBODIMENTS

Figure 1:
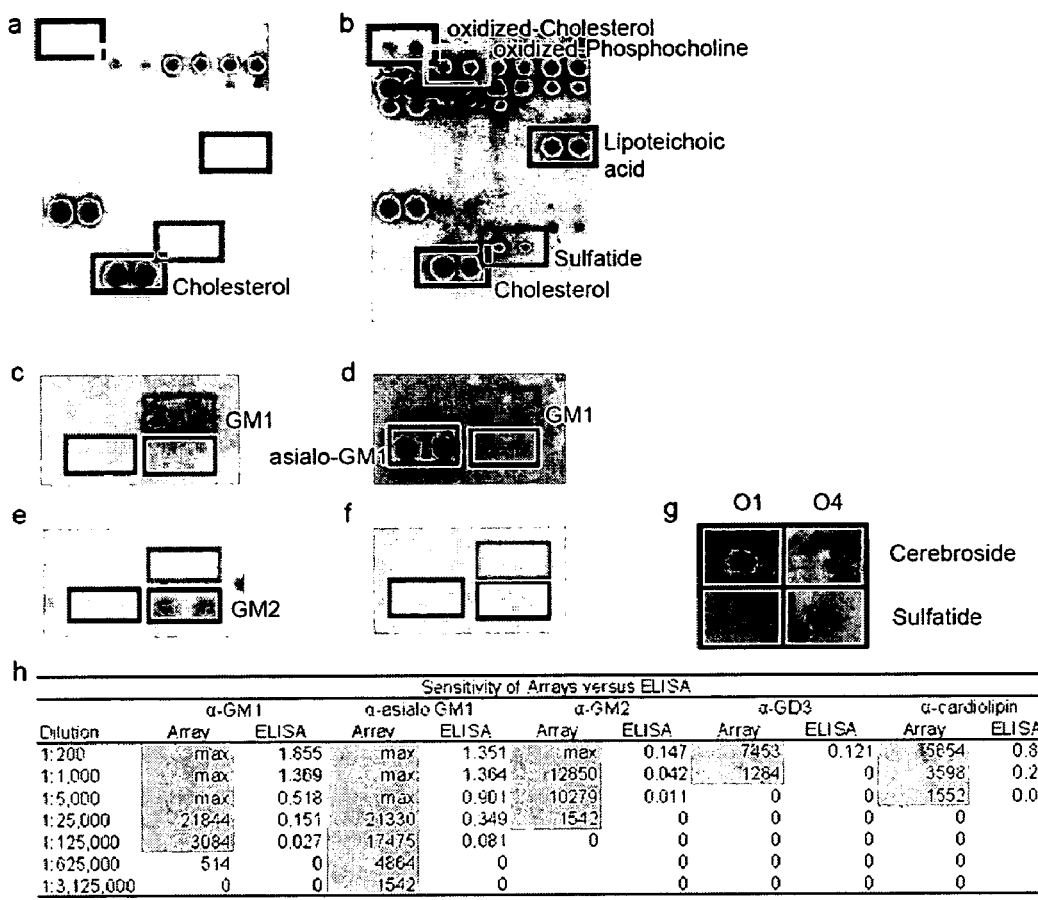
FIG. 1a-1h. Lipid microarrays. Lipid arrays were generated by using a robot to spray purified lipids to form ordered arrays on the surface of PVDF membranes attached to the surface of microscope slides. Arrays were probed with dilutions of sera or CSF samples followed by a horseradish peroxidase (HRP)-conjugated anti-IgG antibody, and chemiluminescence was used to detect antibody binding. (a-b) Individual lipid arrays were probed with 1:10 dilutions of CSF from another neurological disease control patient (a) and a relapsing-remitting MS patient (b). (c-g) Array validation. Individual arrays were incubated with polyclonal antibodies specific for GM1 (c), asialo-GM1 (d), GM2 (e) or secondary antibody alone (f). Individual arrays were also incubated with the monoclonal antibodies O1 specific for cerebroside and O4 specific for sulfatide (g). (h) Comparison of lipid arrays with ELISA. Identical samples of diluted sera containing antibodies specific for 5 different lipids were assayed using lipid arrays and ELISA. Positive values for array and ELISA analyses are highlighted. The minimum limit for positive reactivity was set at 0.100 for ELISA and 1000 digital chemiluminescence units for the lipid array results.

Compositions and methods are provided for multiplex profiling of lipid binding ligands, which ligands may include proteins, such as antibodies, having specific binding reactivity to one or more lipids, where lipids can include glycolipids, phospholipids, triglycerides, etc. In some embodiments, a set of lipids are arrayed on a substantially planar, hydrophobic substrate, which substrate may be a membrane. The arrays are then contacted with a sample containing suspected ligands. The presence of ligands bound to the lipids is then determined.

The lipid arrays of the present invention utilize a substantially planar, hydrophobic surface. Such a surface typically provides a flat surface for lipid binding, and may be in the absence of three dimensional features to contain the lipids, i.e. corrals, microtiter wells, and the like. In the arrays of the invention, the lipids are typically not present in an organized membrane such as a lipid bilayers or micelle. The lipid of interest is generally spotted onto the substrate in the absence of other lipids, in the absence of a lipid bilayer membrane, or a lipid monolayer vesicle, or equivalent structure.

The methods and compositions are useful in a variety of clinical and research applications. Such applications include the detection and/or quantitation of antibodies in a sample that have antigenic specificity for a lipid antigen of interest, which may include tumor antigens; viral antigens, bacterial antigens; parasitic antigens; environmental antigens; allergens; autoantigens; etc. Samples may be clinical samples, e.g. blood, lymph, cerebrospinal fluid, synovial fluid, and the like.

In one embodiment of the invention, lipid-specific antibody specificity profiles are determined through the binding of antibodies from a patient sample to lipids, including lipids present in an array, lipids present in ELISA screening assays, and the like, where the lipids correspond to potential epitopes of antigens. Small amounts of the sample are sufficient to screen a large number of different lipids. An array will comprise individual spots of lipids, and may further comprise other autoantigens.

In the case of autoimmune disease an antibody lipid-specificity profile provides a means of diagnosis, prognosis, monitoring and/or predicting the patient response to treatment, where the treatment may be antigen specific, for example in the administration of tolerizing doses of lipids, or modification of regulatory T and NKT cell responses. Treatment may also be antigen-non-specific, for example in the administration and cytolytic treatment directed to B cells; selection of chemotherapeutic agents such as azathioprine primarily targeted to B cells; and the like. The antibody response profile can indicate whether efficacious therapy has been delivered to the patient. Methods of such profiling are detailed in U.S. Patent Application, publication US-2003-0003516-A1, herein specifically incorporated by reference.

The information obtained from the antibody specificity profile is used to monitor treatment, modify therapeutic regimens,. and to further optimize the selection of therapeutic agents. With this approach, therapeutic and/or diagnostic regimens can be individualized and tailored according to the specificity data obtained at different times over the course of treatment, thereby providing a regimen that is individually appropriate. In addition, patient samples can be obtained at any point during the treatment process for analysis.

In other embodiments, the lipid arrays find use in, for example, drug screening assays. Toxins can target a variety of molecules on the surface of a host cell, and certain bacterial toxins, e.g. from the genera *Streptococcus, Bacillus, Clostridium*, and *Listeria*, target cholesterol molecules. A large number of bacterial toxins target carbohydrate-derivatized lipids on the cell surface, often with high specificity. These lipids, glycosylated derivatives of ceramides, referred to as sphingoglycolipids, can be classified into cerebrosides (ceramide monosaccharide), sulfatides (ceramide monosaccharide sulfates), and gangliosides (ceramide oligosaccharides). One of the best-studied examples of toxin-ganglioside interactions is the binding of the toxin produced by *Vibrio cholerae* to the ganglioside GM1. The specificity of toxin-carbohydrate interactions is well demonstrated by differences in the binding epitopes between the tetanus and cholera toxins, where the toxin produced by *Clostridium tetani* binds specifically to the ganglioside GT1b. Lipid microarrays, for example containing gangliosides, may be used for toxin detection, as well as screening of compounds as potential toxin inhibitors.

Mammalian species that provide samples for analysis include canines; felines; equines; bovines; ovines; etc. and primates, particularly humans. Animal models, particularly small mammals, e.g. murine, lagomorpha, etc. may be used for experimental investigations. Animal models of interest include those for models of autoimmunity, cardiac disease, and the like.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Lipids are fatty acid esters, a class of water-insoluble organic molecules. Lipids consist of a polar or hydrophilic head and one to three nonpolar or hydrophobic tails. The hydrophobic tail consists of one to four fatty acids. These are usually unbranched hydrocarbon chains which may be saturated or unsaturated, although branch-chain sphingoid bases have been described. The chains are usually 14-24 carbon groups long. Biologically relevant lipids are often glycolipids, phospholipids, or sterols. In glycolipids, the head group comprises an oligosaccharide of from 1 to 15 saccharide residues. Phospholipids comprise a negatively charged phosphate group. Sterol head groups comprise a planar steroid ring, for example, cholesterol.

Glycolipids comprise a lipid and saccharide group, which may be a hexose or a pentose, and may be a mono-, di-, tri-, oligo, or polysaccharide, or a derivative thereof. Sugars of interest include allose, altrose, glucose, mannose, gulose, idose, galactose, talose, fructose, maltose, lactose, and sucrose. The linkage between the sugar and the lipid may be at any of the O atoms, and the linkage may be in the alpha or beta configuration.

Lipids of interest include, inter alia, ceramides; gangliosides; cerebrosides, sphingosines; sulfatide; sphingomyelin; phosphatidylamines and phosphatidyl alcohols, such as phosphatidylinositol, phosphatidylserine, phosphatidylcholine, etc.; lipopolysaccharides; LDLs, cholesterols; and the like. In some embodiments, the arrays of the invention comprise at least one, at least two, at least three, at least five, at least ten or more lipids or related lipids selected from Table 1. Oxidized forms of lipids are of interest, e.g. in the profiling of atherosclerosis, including oxidized or non-oxidized lipids present in serum such as LDLs, and demyelinating diseases, including myelin derived lipids. Lipids may be autoantigens; or may be other lipids of interest for various purposes. Where the lipids are antigens, the antigens may comprise one or more epitopes.

Substrate

As used herein the term "substrate" refers to any surface to which the lipids are arrayed in defined, specific geographic locations. The array may comprise a plurality of different lipids, which are patterned in a pre-determined manner, including duplicates of single probe types and combinations of different probes in a given spot.

A preferred substrate is a hydrophobic membrane, having a pore size of from about 0.05 to 5 µm. The membrane is stable to organic solvents., in which the lipids are dissolved for spotting. Such membranes may be affixed to any convenient support, for example a glass slide; cylinder, etc. to provide for ease of use. A planar or planar three-dimensional geometry is preferred.

In one embodiment of the invention, the substrate comprises a planar surface, and the lipids are spotted on the surface in an array. The lipid spots on the substrate can be any convenient shape, but will often be circular, elliptoid, oval or some other analogously curved shape. The spots can be arranged in any convenient pattern across or over the surface of the support, such as in rows and columns so as to form a grid, in a circular pattern, and the like, where generally the pattern of spots will be present in the form of a grid across the surface of the solid support.

The lipids can be prepared using any convenient means, and often commercially available. Prior to spotting, the lipids are dissolved in a suitable solvent, typically an organic solvent, e.g. chloroform, methanol, etc., where the solvent may be volatile. Usually care will be taken prior to spotting to maintain the lipids in a low oxygen atmosphere, e.g. in a capped tube under $N_2$. The lipids are used as a suitable concentration, which may be empirically determined, for example in a solution of from 1 µg/ml to about 1 mg/ml.

In one embodiment, an automated spotting device is utilized, e.g. Perkin Elmer BioChip Arrayer. A number of contact and non-contact microarray printers are available and may be used to print the lipids on a substrate. Other approaches include ink jet-based printing and microfluidic platforms. Contact printers are commercially available from TeleChem International. Of particular interest is the use of TLC sampler (Camag automatic TLC Sampler 4 (ATS4), which sprays small volumes of liquid under nitrogen gas.

The total number of lipid spots on the substrate will vary depending on the desired use of the array, as well as the number of control spots, calibrating spots and the like, as may be desired. Generally, the pattern present on the surface of the support will comprise at least about 2 distinct spots, usually at least about, 10 distinct spots, and more usually at least about 25 distinct spots, where the number of spots will usually not exceed about 1000 distinct spots, and more usually will not exceed about 500 distinct spots. Each distinct lipid composition may be present in duplicate or more to provide an internal correlation of results. The spot will usually have an overall circular dimension and the diameter will range from about 10 to 5,000 µm, usually from about 100 to 1000 µm. The density of spots on the substrate surface will usually be at least about $1/cm^2$, and may be $5/cm^2$; $10/cm^2$, or greater.

Antibodies and Autoantibodies

In some embodiments of the invention, the ligands tested for lipid binding are antibodies. The portion of the antigen bound by the antibody is referred to as an epitope. An individual antigen typically contains multiple epitopes, although there are instances in which an antigen contains a single epitope. As used herein, an epitope is that portion of the antigen which is sufficient for high affinity binding. The epitope of a lipid may be the hydrophobic tail, or more commonly, the hydrophilic head region.

Autoreactive antibodies, or autoantibodies, bind with high affinity to molecules present in the host, usually molecules that are normally present in the host, e.g. in autoimmune disease or tumor antigens in the case of certain cancers. The initiating immunogen may be the autoantigen, or may be a cross-reactive molecule with the autoantigen.

For the purposes of the invention, panels of autoantigens or autoantigen epitopes may be used for screening purposes, where the panel reflects the different epitopes associated with a particular disease. Antigen epitope panels of interest include panels optimized for specific diseases of interest. An array of antigens will comprise one or more different antigenic molecules, i.e. a protein, lipid, polysaccharide, polynucleotide molecule, and will usually comprise two or more different antigens, more usually three or more antigens, and may comprise as many as five to ten different antigens, or more. Each antigen may be represented by one or more different epitopes, usually three or more different epitopes, more usually five or more, and may be as many as ten to twenty different epitopes.

For the purposes of the invention, arrays of autoantigens and autoantigen-derived epitopes can be used to determine a patient's antibody specificity profile for the identification or determination of: patients likely to develop disease; patients likely to develop more or less severe disease; patients likely to respond to a particular therapy, or to have an adverse event related to a particular therapy; patient-specific therapy; and whether a particular therapeutic intervention has been successful, unsuccessful, or detrimental.

An autoantigen array comprises the various autoantigens either known to be associated with disease, suspected to be associated with a particular disease, or a library of potential autoantigens. Panels or arrays may be specific for a disease, e.g. multiple sclerosis, arthritis, SLE, etc., for a class of diseases, e.g. transplant related disorders, allergic disorders, etc., or may be a broad based antigenic panel or array for multiple diseases, while in another instance may include a library of unknown antigens to identify targets of the antibody response in patients with a disease. An autoantigen array consisting of panels of autoantigens may be used for screening purposes, where the panel reflects the different epitopes associated with a particular disease. Antigen epitope panels of interest include panels optimized for specific diseases of interest.

Lipids, and particularly glycolipids, that have been associated with autoimmune disease include gangliosides and sulfatides in association with demyelinating disease. For example, antibodies to >20 different glycolipids have now been associated with a wide range of clinically identifiable acute and chronic neuropathy syndromes. Acute motor axonal neuropathy has been associated with antibodies to GM1, GD1a, GM1b and GalNAc-GD1a. The cranial, bulbar and sensory variants of GBS has been associated with antibodies to the disialylated gangliosides GQ1b, GT1a, GD1b and GD3. Miller-Fisher syndrome has been associated with anti-GQ1b antibodies Lipids found in bacterial pathogens may act as mimics to initiate disease, e.g. *Campylobacter jejuni*. (see Willison et al. (2002) Brain 125:2591-2625, December 2002, herein specifically incorporated by reference).

Relating to IDDM, GM2-1 is a pancreatic islet monosialoganglioside, which is an islet-specific component whose expression is metabolically regulatable and represents one of the target antigens of cytoplasmic islet cell antibodies (Dotta et al. (1995) Diabetologia 38:117-1121). Sulfatide has also been associated with IDDM, and anti-sulfatide antibodies have been found in patients with newly diagnosed insulin-dependent diabetes mellitus (Buschard et al. (1996) Diabetologia 39 ISSN: 0012-186X).

Lipids become autoantigen targets in systemic lupus erythematosus (SLE). In SLE, a subset of patients develop autoantibodies targeting cardiolipin and certain phospholipids. Such anti-cardiolipin, anti-phospholipid and "lupus anticoagulant" antibodies alter the coagulation cascade making SLE patients hypercoagulable and prone to develop deep vein thromboses (DVTs) and arterial thromboses. Such autoantibodies are also associated with increased rates of and recurrent spontaneous miscarriage of pregnancies. (see Kotzin et al. (1996) *Cell* 85:303-306 for a review of the disease)

Lipid autoantigens have also been associated with atherosclerosis. 2-Glycoprotein I (2-GPI) is a major antigen for antiphospholipid antibodies present in patients with antiphospholipid syndrome (APS). 2-GPI specifically binds to oxidized low-density lipoprotein (oxLDL) and the 2-GPI-oxLDL complex may be targeted by anti-2-GPI antibodies. Appearance of autoantibodies against a complex of 2-GPI and oxLig-1 are highly associated with a history of arterial thrombosis. Serum oxLDL-2-GPI complex and their IgG immune complexes are also risk factors arterial thrombosis in APS patients (Matsura et al. (2003) Immunobiology 207:17-22).

Immune related diseases include: autoimmune diseases in which the immune response aberrantly attacks self-antigens, examples of which include but are not limited to multiple sclerosis (MS), acute disseminated encephalomyelitis (ADEM), rheumatoid arthritis (RA), type I autoimmune diabetes (IDDM), atherosclerosis, systemic lupus erythematosus (SLE), anti-phospholipid antibody syndrome, Guillain-Barre syndrome (GBS) and its subtypes acute inflammatory demyelinating polyradiculoneuropathy, and the autoimmune peripheral neuropathies; allergic diseases in which the immune system aberrantly attacks molecules such as pollen, dust mite antigens, bee venom, peanut oil and other foods, etc.; and tissue transplant rejection in which the immune system aberrantly attacks antigens expressed or contained within a grafted or transplanted tissue, such as blood, bone marrow cells, or solid organs including hearts, lungs, kidneys and livers; and the immune response against tumors. Samples are obtained from patients with clinical symptoms suggestive of an immune-related disease or with an increased likelihood for developing such a disease based on family history or genetic testing.

Binding Analysis

The arrays of the present invention can be used in various assays to detect the presence of lipid-specific ligands. The candidate ligands may be present in a variety of samples. Ligands of interest are biologically active agents that encompass numerous chemical classes, primarily organic molecules, which may include proteins, organometallic molecules, inorganic molecules, genetic sequences, etc. An important aspect of the invention is to analyze patient samples, evaluate candidate drugs, including lipid binding inhibitor molecules, and provide for patient profiles. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Lipids autoantigens are produced or generated in the animal (for example, at some time during the life of the animal), and may be modified by oxidation, enzymatic reactions, breakdown and can be present in the animal non-physiologically or in non-physiological amounts or forms. The term "non-physiological" or "non-physiologically" when used to describe the lipids of this invention means a departure or deviation from the normal role or process in the animal for that lipid. When referring to the lipid "associated with a disease" or "involved in a disease" it is understood to mean that the lipid may be modified in form or structure and thus be unable to perform its physiological role or process; or may be involved in the pathophysiology of the condition or disease either by inducing the pathophysiology, mediating or facilitating a pathophysiologic process; and/or by being the target of a pathophysiologic process. For example, in autoimmune disease, the immune system aberrantly attacks lipids and other biomolecules causing damage and dysfunction of cells and tissues in which the lipid is present. Alternatively, the lipid can itself be expressed at non-physiological levels and/or function non-physiologically.

Certain microbial infections may evoke immunity against certain microbial lipids that stimulate a cross-reactive autoimmune response against a self lipid in individuals expressing major histocompatibility complex alleles capable of binding that lipid. For example, the lipopolysaccharide (LPS) component of *C. jejuni* resembles self-gangliosides, and can trigger an autoimmune response that results in *Guillain Barré syndrome*.

Test compounds include all of the classes of molecules described above, and may further comprise samples of unknown content. Of interest are complex mixtures of naturally occurring compounds derived from natural sources. While many samples will comprise compounds in solution, solid samples that can be dissolved in a suitable solvent may also be assayed. Samples of interest include compounds being assessed for potential therapeutic value, i.e. drug candidates.

The term "samples" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection; usually from about 0.1 µl to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Ligands are screened for specificity of lipid binding by adding the agent to one or more lipids, e.g. in an array of the present invention. The binding is measured, desirably normalized, and the resulting information may then be evaluated by comparison to reference datasets, positive and negative controls, and the like. Generally assays will include various negative and positive controls, as known in the art. These may include positive controls of "spiked" samples with known ligands, patients with known disease, and the like. Negative controls include samples from normal subjects, animal serum, and the like.

In a typical assay, a sample is physically contacted with the lipids under conditions that permit high affinity binding, but that minimize non-specific interactions. In one embodiment, samples are brought into contact with an array. The array is washed free of unbound material, and the presence of bound ligands is detected, and correlated with the cognate lipid.

The means for identifying the lipids within the array that bind to the ligands utilize methods for detection that are known in the art. Those methods of identification may include pre-labeling the sample directly or indirectly; adding a second stage reagent that binds to the ligand or to an indirect label, e.g. labeled goat anti-human serum, rat anti-mouse, and the like. Other methods of identification include analysis of addressable elements such as beads, nanoparticles, tags, cleavable tags and other physical properties of or conferred upon the elements within the array. Varying concentrations of a single lipid may be present in order to facilitate quantitation of the bound antibody.

Antibody or other ligand binding to lipids contained on the array can be detected using a variety of methods, including chemiluminescence, fluorescence, fluorescence at infared and farred wavelengths, radioactivity, and other tags and labels. It is also possible to utilize indirect labels, including haptens such as digoxin and digoxigenin, biotin, etc., where a second stage binding partner, e.g. avidin, anti-digoxin antibody, etc., may be labeled with an enzyme, e.g. horseradish peroxidase, radioactive label, etc. and used to detect antibody or ligand binding to a lipid contained on the array. Chemiluminescent labels include N-(4-Aminobutyl)-N-ethylisoluminol; Luminol; 4-Aminophthalhydrazide monohydrate; Bis(2-carbopentyloxy-3,5,6-trichlorophenyl) oxalate; 9,10-Bis (phenylethynyl)anthracene; 5,12-Bis(phenylethynyl) naphthacene; 2-Chloro-9,10-bis(phenylethynyl)anthracene; 1,8-Dichloro-9,10-bis(phenylethynyl)anthracene; Lucifer Yellow; 2,4,5-Triphenylimidazole; 9,10-Diphenylanthracene; Rubrene, Tetrakis(dimethylamino)ethylene; etc.

Two-channel labeling of different ligands can be utilized in binding to the same or to separate arrays, in order to assay the level of binding in a sample compared to a control sample. From the ratio of one color to the other, for any particular array element, the relative abundance of ligands with a particular specificity in the two samples can be determined. In addition, comparison of the binding of the two samples provides an internal control for the assay. Competitive assays are well known in the art, where a competing ligand of known specificity, or lipid, may be included in the binding reaction.

Detection may also occur using methods that do not require labeling. Examples include detection of changes in charge or mass of the bound self-lipid using methods or devices such as single electron transistors, proteins applied to carbon nanotubes or meshworks of nanotubes, surface plasmon resonance, atomic force microscopy, and other methods known to those of skill in the art.

A plurality of assays may be run in parallel with different concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

For profiling patient samples, the lipid binding specificity of antibodies present in a patient sample may be determined based binding of a patient sample lipids, usually lipid autoantigens, which lipid autoantigens may include oxidized lipids; gangliosides; sphingomyelin; PGPC; etc., as described herein.

The autoantibody profile may be generated from a biological sample using any convenient protocol. While a variety of different manners of generating expression profiles are known, one representative and convenient type of protocol for generating expression profiles is array based antibody binding. Following obtainment of the profile from the sample being assayed, the profile is compared with a reference or control profile to make a diagnosis regarding the phenotype of the patient from which the sample was obtained/derived. Typically a comparison is made with a sample from an unaffected, normal source. Additionally, a reference or control profile may be a profile that is obtained from a cell/tissue known to be positive for disease, and therefore may be a positive reference or control profile.

In one embodiment of the invention, synovial fluid, cerebrospinal fluid, blood samples, or samples derived from blood, e.g. plasma, serum, etc. are assayed for the presence of autoantibodies. Such antibodies may be detected through specific lipid binding. Various formats find use for such assays, including antibody arrays; ELISA and RIA formats; binding of labeled antibodies in suspension/solution and detection by flow cytometry, mass spectroscopy, and the like. Detection may utilize one or a panel of lipids, e.g. specific for at least about 1, 2, at least about 3, at least about 4, 5, at least about 10 or more different lipids.

In certain embodiments, the obtained profile is compared to a single reference/control profile to obtain information regarding the phenotype of the sample being assayed. In yet other embodiments, the obtained expression profile is compared to two or more different reference/control profiles to obtain more in depth information regarding the phenotype of the assayed sample. For example, the obtained expression profile may be compared to a positive and negative reference profile to obtain confirmed information regarding whether the sample has the phenotype of interest.

The difference values, i.e. the difference in antibody binding may be performed using any convenient methodology, where a variety of methodologies are known to those of skill in the array art, e.g., by comparing digital images of the profiles, by comparing databases of expression data, etc. Patents describing ways of comparing profiles include, but are not limited to, U.S. Pat. Nos. 6,308,170 and 6,228,575, the disclosures of which are herein incorporated by reference.

Methods of profiling may also include, without limitation, utilizing a dataset to generate a predictive model, and inputting test sample data into such a model in order to classify the sample according to an autoimmune disease classification, where the classification is selected from the group consisting of a disease classification, a (control) healthy classification; progressive disease, relapsing disease, etc. and classifying the sample according to the output of the process. In some embodiments, such a predictive model is used in classifying a sample obtained from a mammalian subject by obtaining a dataset associated with a sample, wherein the dataset comprises at least one, at least two, three, or at least four, or at least five lipid markers.

Formats for human patient sampling include time courses that follow the progression of disease, comparisons of different patients at similar disease stages, e.g. early onset, acute stages, recovery stages, etc.; tracking a patient during the course of response to therapy, including drug therapy, vaccination and the like. Data from animals, e.g. mouse, rat, rabbit, monkey, etc. may be compiled and analyzed in order to provide databases detailing the course of disease, antigens involved in diseases, etc. Biological samples which may be collected include blood and derivatives therefrom, e.g. serum, plasma, fractions of plasma,.etc. Other sources of samples are body fluids such as synovial fluid, lymph, cerebrospinal fluid (CSF), bronchial aspirates, and may further include saliva, milk, urine, and the like. Antibodies may also be obtained from the appropriate lymphocytes, which may be collected from blood, tissues such as spleen, thymus, lymph nodes, fetal liver, tissues at the site of autoimmune lesions, e.g. pancreas, joints, kidneys, cerebrospinal fluid, brain lesions, etc.

In implementations of lipid microarrays where high throughput molecular and functional profiling is desired, an appropriate method of high throughput data acquisition is required for enablement. Microarrays can be scanned to detect the presence of bound ligands, e.g. by using autoradiography, phosphoimaging, light microscopy, scanning laser microscope, by fluorimetry, a modified ELISA plate reader, laser-based microarray scanners, etc. For any particular array element, the ratio of the signal with one label may be compared to the signal from a control ligand or signal, and the relative abundance determined.

Conditions for Analysis and Therapy

The compositions and methods of the invention find use in combination with a variety of conditions. Among these are autoimmune diseases having a lipid component. It has been found that demyelinating autoimmune diseases, in particular, have a lipid component, as does IDDM, SLE, coronary artery disease, etc.

Demyelinating diseases may be characterized according to the presence of autoantibodies specific for lipids associated with the nervous system, and in particular with myelin. Myelin sheaths, which cover many nerve fibers, are composed of lipoprotein layers formed in early life. Myelin formed by the oligodendroglia in the CNS differs chemically and immunologically from that formed by the Schwann cells peripherally, but both types have the same function: to promote transmission of a neural impulse along an axon. Demyelinating diseases include those that affect the central nervous system, and those that affect the peripheral nervous system. CNS conditions include multiple sclerosis, and the animal model EAE, which are slowly progressive CNS diseases characterized by disseminated patches of demyelination in the brain and spinal cord, resulting in multiple and varied neurologic symptoms and signs, usually with remissions and exacerbations.

Plaques of demyelination, with destruction of oligodendroglia and perivascular inflammation, are disseminated throughout the CNS, primarily in the white matter, with a predilection for the lateral and posterior columns (especially in the cervical and dorsal regions), the optic nerves, and periventricular areas. Tracts in the midbrain, pons, and cerebellum are also affected as is gray matter in the cerebrum and spinal cord. Cell bodies and axons are usually preserved, especially in recent lesions. Later, axons may be destroyed, especially in the long tracts, and a fibrous gliosis makes the tracts appear sclerotic. Recent and old lesions may coexist. Chemical changes in lipid and protein constituents of myelin occur in and around the plaques.

Multiple sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g. partial blindness and pain in one eye (retrobulbar optic neuritis), dimness of vision, or scotomas. Other common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive (primary progressive MS, PPMS). Relapsing remitting MS (RR MS) is characterized clinically by relapses and remissions that occur over months to years, with partial or full recovery of neurological deficits between attacks. Such patients manifest approximately 1 attack, or relapse, pre year. Over 10 to 20 years, approximately 50% of RR MS patients develop secondary progressive MS (SP MS) which is characterized by incomplete recovery between attacks and accumulation of neurologic deficits resulting in increasing disability.

Diagnosis is indirect, by deduction from clinical, radiographic (brain plaques on magnetic resonance [MR] scan), and to a lesser extent laboratory (oligoclonal bands on CSF analysis) features. Typical cases can usually be diagnosed confidently on clinical grounds. The diagnosis can be suspected after a first attack. Later, a history of remissions and exacerbations and clinical evidence of CNS lesions disseminated in more than one area are highly suggestive.

MRI, the most sensitive diagnostic imaging technique, may show plaques. It may also detect treatable nondemyelinating lesions at the junction of the spinal cord and medulla (eg, subarachnoid cyst, foramen magnum tumors) that occasionally cause a variable and fluctuating spectrum of motor and sensory symptoms, mimicking MS. Gadolinium-contrast enhancement can distinguish areas of active inflammation from older brain plaques. MS lesions may also be visible on contrast-enhanced CT scans; sensitivity may be increased by giving twice the iodine dose and delaying scanning (double-dose delayed CT scan).

Treatments for MS include interferon β (Avonex, Betaseron, Rebif), Copaxone (Glatiramer acetate), and anti-VLA4 (Tysabri, natalizumab), which reduce relapse rate and to date have only exhibited a modest impact on disease progression. MS is also treated with immunosuppressive agents including methylprednisolone, other steroids, methotrexate, cladribine and cyclophosphamide. Many biological agents, such as anti-IFNgamma antibody, CTLA4-Ig (Abetacept), anti-CD20 (Rituxan), and other anti-cytokine agents are in clinical development for MS.

Peripheral neuropathies include Guillain-Barre syndrome (GBS) with its subtypes acute inflammatory demyelinating polyradiculoneuropathy, acute motor axonal neuropathy, acute motor and sensory axonal neuropathy, Miller Fisher syndrome, and acute pandysautonomia; chronic inflammatory demyelinating polyneuropathy (CIDP) with its subtypes classical CIDP, CIDP with diabetes, CIDP/monoclonal gammopathy of undetermined significance (MGUS), sensory CIDP, multifocal motor neuropathy (MMN), multifocal acquired demyelinating sensory and motor neuropathy or Lewis-Sumner syndrome, multifocal acquired sensory and motor neuropathy, and distal acquired demyelinating sensory neuropathy; IgM monoclonal gammopathies with its subtypes Waldenstrom's macroglobulinemia, myelin-associated glycoprotein-associated gammopathy, polyneuropathy, organomegaly, endocrinopathy, M-protein, skin changes syndrome, mixed cryoglobulinemia, gait ataxia, late-onset polyneuropathy syndrome, and MGUS.

SLE.

Systemic lupus erythematosus (SLE) is an autoimmune disease characterized by polyclonal B cell activation, which results in a variety of anti-protein and non-protein autoantibodies (see Kotzin et al. (1996) *Cell* 85:303-306 for a review of the disease). These autoantibodies form immune complexes that deposit in multiple organ systems, causing tissue damage. SLE is a difficult disease to study, having a variable disease course characterized by exacerbations and remissions. For example, some patients may demonstrate predominantly skin rash and joint pain, show spontaneous remissions, and require little medication. The other end of the spectrum includes patients who demonstrate severe and progressive kidney involvement (glomerulonephritis) that requires therapy with high doses of steroids and cytotoxic drugs such as cyclophosphamide.

Multiple factors may contribute to the development of SLE. Several genetic loci may contribute to susceptibility, including the histocompatibility antigens HLA-DR2 and HLA-DR3. The polygenic nature of this genetic predisposition, as well as the-contribution of environmental factors, is suggested by a moderate concordance rate for identical twins, of between 25 and 60%.

Many causes have been suggested for the origin of autoantibody production. Proposed mechanisms of T cell help for anti-dsDNA antibody secretion include T cell recognition of DNA-associated protein antigens such as histones and recognition of anti-DNA antibody-derived peptides in the context of class II MHC. The class of antibody may also play a factor. In the hereditary lupus of NZB/NZW mice, cationic IgG2a anti-double-stranded (ds) DNA antibodies are pathogenic. The transition of autoantibody secretion from IgM to IgG in these animals occurs at the age of about six months, and T cells may play an important role in regulating the IgG production.

Disease manifestations result from recurrent vascular injury due to immune complex deposition, leukothrombosis, or thrombosis. Additionally, cytotoxic antibodies can mediate autoimmune hemolytic anemia and thrombocytopenia, while antibodies to specific cellular antigens can disrupt cellular function. An example of the latter is the association between anti-neuronal antibodies and neuropsychiatric SLE.

Atherosclerotic plaque consists of accumulated intracellular and extracellular lipids, smooth muscle cells, connective tissue, and glycosaminoglycans. The earliest detectable lesion of atherosclerosis is the fatty streak, consisting of lipid-laden foam cells, which are macrophages that have migrated as monocytes from the circulation into the subendothelial layer of the intima, which later evolves into the fibrous plaque, consisting of intimal smooth muscle cells surrounded by connective tissue and intracellular and extracellular lipids.

Interrelated hypotheses have been proposed to explain the pathogenesis of atherosclerosis. The lipid hypothesis postulates that an elevation in plasma LDL levels results in penetration of LDL into the arterial wall, leading to lipid accumulation in smooth muscle cells and in macrophages. LDL also augments smooth muscle cell hyperplasia and migration into the subintimal and intimal region in response to growth factors. LDL is modified or oxidized in this environment and is rendered more atherogenic. The modified or oxidized LDL is chemotactic to monocytes, promoting their migration into the intima, their early appearance in the fatty streak, and their transformation and retention in the subintimal compartment as macrophages. Scavenger receptors on the surface of macrophages facilitate the entry of oxidized LDL into these cells, transferring them into lipid-laden macrophages and foam cells. Oxidized LDL is also cytotoxic to endothelial cells and may be responsible for their dysfunction or loss from the more advanced lesion.

The chronic endothelial injury hypothesis postulates that endothelial injury by various mechanisms produces loss of endothelium, adhesion of platelets to subendothelium, aggregation of platelets, chemotaxis of monocytes and T-cell lymphocytes, and release of platelet-derived and monocyte-derived growth factors that induce migration of smooth muscle cells from the media into the intima, where they replicate, synthesize connective tissue and proteoglycans, and form a fibrous plaque. Other cells, e.g. macrophages, endothelial cells, arterial smooth muscle cells, also produce growth factors that can contribute to smooth muscle hyperplasia and extracellular matrix production.

Endothelial dysfunction includes increased endothelial permeability to lipoproteins and other plasma constituents, expression of adhesion molecules and elaboration of growth factors that lead to increased adherence of monocytes, macrophages and T lymphocytes. These cells may migrate through the endothelium and situate themselves within the subendothelial layer. Foam cells also release growth factors and cytokines that promote migration of smooth muscle cells and stimulate neointimal proliferation, continue to accumulate lipid and support endothelial cell dysfunction. Clinical and laboratory studies have shown that inflammation plays a major role in the initiation, progression and destabilization of atheromas.

The "autoimmune" hypothesis postulates that the inflammatory immunological processes characteristic of the very first stages of atherosclerosis are initiated by humoral and cellular immune reactions against an endogenous antigen. Human Hsp60 expression itself is a response to injury initiated by several stress factors known to be risk factors for atherosclerosis, such as hypertension. Oxidized LDL is another candidate for an autoantigen in atherosclerosis. Antibodies to oxLDL have been detected in patients with atherosclerosis, and they have been found in atherosclerotic lesions. T lymphocytes isolated from human atherosclerotic lesions have been shown to respond to oxLDL and to be a major autoantigen in the cellular immune response. A third autoantigen proposed to be associated with atherosclerosis is 2-Glycoprotein I (2GPI), a glycoprotein that acts as an anticoagulant in vitro. 2GPI is found in atherosclerotic plaques, and hyper-immunization with 2GPI or transfer of 2GPI-reactive T cells enhances fatty streak formation in transgenic atherosclerotic-prone mice.

Infections may contribute to the development of atherosclerosis by inducing both inflammation and autoimmunity. A large number of studies have demonstrated a role of infectious agents, both viruses (cytomegalovirus, herpes simplex viruses, enteroviruses, hepatitis A) and bacteria (*C. pneumoniae, H. pylori*, periodontal pathogens) in atherosclerosis. Recently, a new "pathogen burden" hypothesis has been proposed, suggesting that multiple infectious agents contribute to atherosclerosis, and that the risk of cardiovascular disease posed by infection is related to the number of pathogens to which an individual has been exposed. Of single micro-organisms, *C. pneumoniae* probably has the strongest association with atherosclerosis.

These hypotheses are closely linked and not mutually exclusive. Modified LDL is cytotoxic to cultured endothelial cells and may induce endothelial injury, attract monocytes and macrophages, and stimulate smooth muscle growth. Modified LDL also inhibits macrophage mobility, so that once macrophages transform into foam cells in the subendothelial space they may become trapped. In addition, regenerating endothelial cells (after injury) are functionally impaired and increase the uptake of LDL from plasma.

Atherosclerosis is characteristically silent until critical stenosis, thrombosis, aneurysm, or embolus supervenes. Initially, symptoms and signs reflect an inability of blood flow to the affected tissue to increase with demand, e.g. angina on exertion, intermittent claudication. Symptoms and signs commonly develop gradually as the atheroma slowly encroaches on the vessel lumen. However, when a major artery is acutely occluded, the symptoms and signs may be dramatic.

Currently, due to lack of appropriate diagnostic strategies, the first clinical presentation of more than half of the patients with coronary artery disease is either myocardial infarction or death. Further progress in prevention and treatment depends on the development of strategies focused on the primary inflammatory process in the vascular wall, which is fundamental in the etiology of atherosclerotic disease.

Therapeutic Methods

Figure 7:
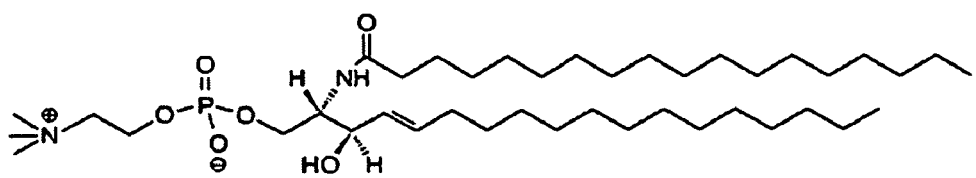
FIG. 7. Structure of sphingomyelin and 1-palmitoyl-2-glutaroyl-sn-glycero-3-phosphocholine (PGPC).
Figure 7:
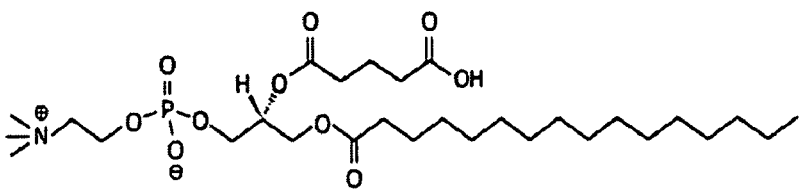

Lipids find use in the treatment of autoimmune disease, where lipids tolerogenic for the disease process are administered to a patient using a tolerizing regimen. In one embodiment, lipids involved in disease may be identified by the methods described herein. In such methods, a patient sample comprising antibodies is contacted with a lipid array according to the present invention, and the binding specificity of the sample is determined by measuring the binding to specific lipids. Lipids this selected are disease-associated. Alternatively, naturally occurring lipids or analogs thereof are selected as tolerogenic candidates based on similarity to known autoantigens, similarity to known tolerogens, e.g. sphingomyelin, PGPC (shown in FIG. 7), and the like.

Alternatively, lipids suspected of disease association may be determined by measuring the lipid specific reactivity of samples of antibodies or T cells using methods other than those described herein. Such methods have been described in the art, for example see Sidobre et al. (2002) JI 169: 1340-1348; Nepom (2003) Clinical Immunology 106:1-4; and Godfrey et al. (2004) J. Clin. Invest. 114:1379-1388 for methods of determining T cell reactivity; or Willison et al. (2002) supra.; Buschard et al. (1996) supra.; Matsura et al. (2003) supra., for methods of determining antibody reactivity.

Lipids, including disease associated lipids or analogs thereof, are used to induce tolerance in a patient. Analogs of interest, without limitation, include those analogs that have altered length and/or saturation of the hydrophobic tail region. Other analogs of interest include those that have altered carbohydrate head groups, e.g. different saccharides; additional heterogroups; and altered stereochemistry, such as different alpha or beta linkage of the saccharide to the lipid; and the like. Candidate analogs may be tested for immune reactivity with any of the methods described herein.

In some embodiments, a tolerogenic lipid is related to sphingomyelin, (or ceramide phosphocholine), which comprises a ceramide with a phosphocholine moiety attached to position 1. Various fatty acid chains may be present, for example sphingosine is usually the most abundant long-chain base constituent, together with sphinganine and C20 homologues. Typically, the fatty acids are very-long-chain saturated and monounsaturated, including odd-numbered components. 2-hydroxy acids may be present. Related lipids of interest as tolerogens include 3-O-acyl-D-erythro-sphingomyelin; sphingosine phosphocholine, (or lyso-sphingomyelin); sphingosine-1-phosphate; sphingadiene, sphingolipid phosphocholine linked to the carbohydrate moiety of mono- and digalactosylceramides; ceramide phosphoethanolamine; ceramide phosphoinositol; phytoglycosphingolipid; ceramide phosphoinositol or (myo-inositol-(1-O)-phospho-(O-1)-ceramide); mannosylinositolphosphoceramide; mannosyldiinositolphosphoceramide; ceramide-1-phosphate; etc. In some embodiments, the tolerogen has the structure:

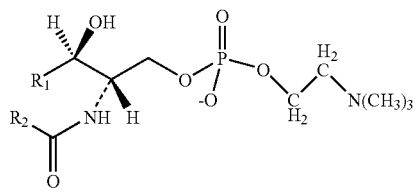

where $R_1$ and $R_2$ are independently selected from a linear or branched $C_3$-$C_{100}$ alkyl; preferably a $C_1$-$C_{30}$ alkyl optionally substituted with halo, hydroxy, alkoxy, amino, alkylamino, dialkylamino, sulfate, or phosphate, and which may by saturated, or mono- or di-unsaturated, e.g. 18:0, 24:0 and 24:1.

In some embodiments, a tolerogenic lipid is related to PGPC (1-palmitoyl-2-gutaroyl-sn-glycero-3-phosphocholine; i.e. lipids comprising a phosphatidylcholine head group. In some embodiments the tolerogen has the structure:

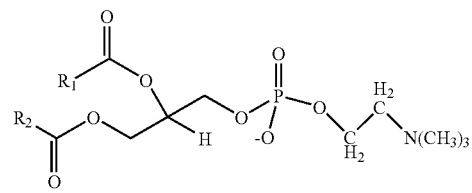

where $R_1$ and $R_2$ are independently selected from a linear or branched $C_3$-$C_{100}$ alkyl; preferably a $C_1$-$C_{30}$ alkyl optionally substituted with halo, hydroxy, alkoxy, amino, alkylamino, dialkylamino, sulfate, or phosphate, and which may by saturated, or contain from 1 to 5, usually 1-2 unsaturated positions, e.g. 18:0, 24:0 and 24:1; and $R_1$ may additionally by $(CH_2)_nCO_2H$, where n is from 1 to 10, usually 1 to 5, and is optionally an ester derivative.

The lipid autoantigen or analog thereof may be administered to a patient to induce tolerance. As the tolerizing effectiveness may vary between lipids, the candidate lipid may be tested for suitability. Methods for assessment include administration of a candidate tolerogen to an animal model for the disease. For example, EAE is demonstrated herein to provide a model model for lipid reactivity in multiple sclerosis; a rabbit model for GBS and related peripheral neuropathies is described by Yuki et al. (2001) Annals of Neurology 49:712-720; autoantibodies to oxidized LDL in a rabbit model are described by Nágila et al. (2000) Journal of Nutrition 130: 2641-2647; and the like. The candidate tolerogen is administered to the animal in a tolerizing dose and regimen, and the effect on the disease is measured.

Candidate tolerogens may also be tested in an in vitro method. Immune cells, e.g. T cells and antigen presenting cells; lymph node cells; bulk splenocytes; peripheral blood lymphocytes; etc. from a patient are contacted with the candidate tolerogen, and the effect on the cells is determined. Where the lipid has a tolerizing effect, the immune cells will respond with decreased production of pro-inflammatory cytokines, e.g; γ-IFN; TNFα, etc. Where a lipid has an immunogenic effect, an increased production of pro-inflammatory cytokines is observed.

Tolerogenic compositions comprise an immunologically effective amount of lipid, as well as any other compatible components, as needed. By "immunologically effective amount" is meant that the administration of that amount to an individual, either in a single dose or as part of a series, is effective for treatment or prevention. This amount varies depending upon the health and physical condition of the individual to be treated, age, individual to be treated (e.g., non-human primate, primate, etc.), the capacity of the individual's immune system to synthesize antibodies, the degree of protection desired, the formulation of the vaccine, the treating clinician's assessment of the medical situation, and other relevant factors. It is expected that the amount will fall in a relatively broad range that can be determined through routine trials. Dosage treatment may be a single dose schedule or a multiple dose schedule (e.g., including booster doses). The tolerogen may be administered in conjunction with other immunoregulatory agents or tolerance-promoting adjuvants.

The effective dose may be empirically determined using animal models and in vitro models, and the dose will depend at least in part on the route of administration. The lipids may be administered orally, in an aerosol spray; by injection, e.g. i.m., s.c., i.p., i.v., etc. In some embodiments, administration by other than i.v. may be preferred.

The lipid dose may be from about 0.1 µg/kg patient weight; about 1 µg/kg; about 10 µg/kg; to about 100 µg/kg. The lipid dose will usually not exceed about 100 mg/kg, and usually not exceed 10 mg/kg.

The lipid tolerogen compositions or individual tolerogens to be administered are administered in a pharmaceutically acceptable excipient, e.g. a lipid based solution or emulsion. The term "pharmaceutically acceptable" refers to an excipient acceptable for use in the pharmaceutical and veterinary arts, which is not toxic or otherwise inacceptable. Examples of suitable lipid-based excipients include mono-, di- and tri-glycerides, especially naturally extracted unsaturated edible oils in hydrogenated form (such as vegetable oil, castor oil, cottonseed oil, corn oil, canola oil, rapeseed oil, peanut oil, sesame seed oil, coconut oil and mixtures thereof).

The compositions may also include a tolerance-promoting adjuvant. Examples of known agents that can be combined with lipid tolerogens to enhance tolerance induction include: (i) interleukins such as IL-4, IL-10, IL-13, TGFbeta and other cytokines and/or chemokines that promote tolerance; (ii) immunoinhibitor oligonucleotide sequences, such as GpG-oligonucleotides (Ho P P et al, *Journal Immunology,* 175(9): 6226-34, 2005); (iii) small molecules identified to promote immune tolerance such as statin drugs (Youssef S, *Nature,* 20(6911):78-84, 2002), anti-histamines (Pedotti et al, *Proc. Natl. Acad. Sci. USA,* 100(4):1867-72, 2003), tryptophan metabolites (Platten M et al, *Science,* 310: 850-5, 2005). The effectiveness of a tolerance-promoting adjuvant may be determined by measuring the T and B cell responses against the lipid antigen as described below for sulfatide, sphingomyelin and PGPC.

The tolerogens may be combined with conventional excipients, such as pharmaceutical grades of mannitol, lactose, starch, magnesium stearate, sodium saccharin, talcum, cellulose, glucose, sucrose, magnesium, carbonate, Tween-20, dimethylsulfoxide (DMSO), and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of tolerogen in these formulations can vary widely, and will be selected primarily based on fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The concentration of tolerogens of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

The tolerogens may be administered in a single dose, or in multiple doses, usually multiple doses over a period of time, e.g. weekly, semi-weekly, monthly etc. for a period of time sufficient to reduce severity of the autoimmune disease, which may comprise 1, 2, 3, 4, 6, 10, or more doses.

The lipids or lipid epitopes recognized by antibodies present in a patient sample, as described above, can be utilized to develop and select antigen or epitope specific therapies that comprise administration of a lipid or lipid epitopes specific therapeutic agent, where the agent is defined by binding of patient antibodies to the addressable elements on the array. The patient antibody specificity profile can be utilized to develop, select, and monitor responses to antigen or epitope specific therapeutic methods.

For these therapies, the antigens administered for purposes of immune suppression may comprise all or a portion of the epitopes identified by antibody. In one embodiment, one or more of the epitopes thus identified are administered, usually two or more, more usually three or more, and may comprise as many as ten or more different epitopes. Individual lipids may be administered. One or more, usually two or more, and as many as three of more different lipid antigens may be thus administered.

Treating, treatment, or therapy of a disease or disorder shall mean slowing, stopping or reversing the disease's progression by administration of a lipid or lipids. In the preferred embodiment, treating a disease means reversing the disease's progression, ideally to the point of eliminating the disease itself. As used herein, ameliorating a disease and treating a disease are equivalent.

Preventing, prophylaxis or prevention of a disease or disorder as used in the context of this invention refers to the administration of a lipid or lipids to prevent the occurrence or onset of a disease or disorder or some or all of the symptoms of a disease or disorder or to lessen the likelihood of the onset of a disease or disorder.

Alternatively, the antibody binding to the array may be correlated with non-antigen-specific therapy. For example, the responsiveness of a patient to immunosuppressive steroids, beta interferons, Copaxone, Tysabri, CTLA4-Ig, methotrexate, cytoreductive therapy, IVIG, and the like may be associated with the presence or absence of lipid specific antibodies. Thus, the methods of the invention are used to guide therapy.

In another embodiment of the invention, the knowledge based methods described above are used to identify patterns of disease, where a particular patient sample can be mapped to a pattern of disease progression. In such cases the suppressive epitopes may comprise not only epitopes currently recognized by patient antibodies, but may anticipate the progression of the disease and administer peptides that are likely to be disease-associated in a later stage of the disease, thus preventing the epitope spread observed in many autoimmune diseases.

Therapeutic administration of lipid tolerogens can be used to both prevent the onset of and to treat established autoimmune disease. For the treatment of established autoimmune disease, patients with the clinical diagnosis of multiple sclerosis, peripheral neuropathies, systemic lupus erythematosus or another autoimmune disease targeting lipids, are administered tolerogens in a tolerizing regimen to reduce the symptoms, severity and/or clinical progression of the disease. For certain autoimmune diseases, biomarkers have been identified that predict which asymptomatic or early-symptomatic individuals will progress to develop definite autoimmune disease. Such biomarkers can include genetic, protein and/or lipid molecules. For example, in patients with clinically isolated syndrome the presence of autoantibodies targeting myelin oligodendrocyte glycoprotein (MOG) and/or myelin basic protein (MBP) predict an increased likelihood for progression to clinically definite multiple sclerosis (Berger et al, New England Journal of Medicine, 349(2):139-45, 2003).

In patients that develop systemic lupus erythematosus, anti-phospholipid, anti-nuclear, anti-DNA, anti-Ro, anti-La and anti-Sm antibodies frequently appear in the blood years before the onset of clinical symptoms and could be utilized to identify patients likely to develop clinical SLE (Arbuckle M R, et al, New England Journal of Medicine, 349(16):1526-33, 2003). Autoantibodies targeting glutamic acid decarboxylase (GAD), a tyrosine phosphatase IA-2 and insulin predict progression of asymptomatic patients to development of clinical autoimmune diabetes (Verge C F et al, Journal Autoimmunity, 9(3):379-83, 1996).

For rheumatoid arthritis, anti-citrullinated protein antibodies (represented by anti-cyclic citrullinated peptide [CCP] reactivity) and rheumatoid factor antibodies predict progression from the asymptomatic state to development of clinical rheumatoid arthritis (Nielen et al, *Arthritis Rheum.* 50(2): 380-6, 2004). Genetic biomarkers that identify individuals with increased likelihood for the development of an autoimmune disease include polymorphisms or mutations in the major histocompatibility complex (such as the shared epitope polymorphism in HLA-DR4 in rheumatoid arthritis), the transcription factors auto immune regulator (AIRE) and forkhead Box P3 (FOXP3) (reviewed in Notarangelo, Advances Immunology, 89:321-70, 2006), and the protein tyrosine phosphatase non-receptor 22 (PTPN22) (reviewed in Serrano N C et al, *Autoimm. Rev.*, 5(3):209-14, 2006).

Thus, in addition to the treatment of patients with established autoimmunity therapeutic administration of tolerogens can be used to prevent the development of autoimmunity in asymptomatic or early symptomatic individuals for which testing for of genetic, protein and/or lipid biomarkers predict progression to a clinical autoimmune disease.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Testing for Anti-Lipid Antibodies with Lipid Microarrays

We developed lipid arrays for simple, large-scale analysis of autoantibodies present in biological fluids such as serum and cerebrospinal fluid (CSF).

Lipid Arrays. Ordered arrays were created with 100 features containing duplicate spots of 50 distinct brain, myelin, and microbial lipids and glycolipids that represent potential targets of the autoimmune response in MS. The lipids printed included ganglioside, sulfatide, cerebroside, sphingomyelin, total brain lipid fractions and microbial lipids (see Table 1 for a list of lipids printed). Arrays were produced using a Camag ATS4 TLC sampler to draw the lipids from sealed vials and spray them under nitrogen gas in spacially-addressable locations on PVDF membranes afixed to microscope slides. Lipid arrays were incubated with diluted serum or CSF samples derived from patients with MS or mice with EAE, and chemiluminescence employed to detect autoantibody binding to specific lipids and glycolipids on the arrays. Images of representative arrays are presented (FIG. 1a-b). As compared to antibody reactivities in CSF derived from another neurological disease (OND) control, antibodies in CSF derived from a patient with MS reacted with lipoteichoic acid and at lower levels with sulfatide, oxidized cholesterol and oxidized-phosphocholine (FIG. 1b).

Array validation and sensitivity analysis. Lipid arrays were validated using polyclonal and monoclonal antibodies with defined specificities. The polyclonal antibodies specific for GM1 bound specifically to GM1, but not to the closely related gangliosides GM2 or asialo-GM1 (FIG. 1c). The polyclonal antibodies raised against asialo-GM1 have previously demonstrated low-level reactivity to GM1, and incubation with lipid arrays demonstrated high-level reactivity against asialo-GM1 and low-level reactivity against GM1 (FIG. 1d). Polyclonal antibodies raised against GM2 specifically bound GM2 (FIG. 1e). The anti-sulfatide antibody O4 and anti-cerebroside antibody O1 specifically bound their corresponding antigen features, differentiating antibody reactivity against lipids that differ by only a sulfate group (FIG. 1g).

Array sensitivity. To assess array sensitivity we performed a direct comparison between lipid arrays and conventional enzyme-linked immunosorbent assay (ELISA). For the 5 specificities tested, lipids arrays were 5 to 25 times more sensitive than the conventional ELISA for detecting anti-lipid antibodies (FIG. 1h).

Lipid arrays enable simple, chemiluminescence-based, multiplex analysis of anti-lipid antibody responses. We believe that the hydrophobic part of the lipid anchors the lipid molecule to the hydrophobic PVDF array surface. The lipid molecules are likely oriented so that the polar regions, such as the sulfate group or glycan molecule, are accessible for antibody binding.

A major challenge in characterizing human autoimmune disease is identifying the antigens against which the immune system is reacting. Knowledge of the specific autoantigen(s) against which an individual patient reacts enables: (i) development of diagnostic tests (Example 2, below), and (ii) administration of individual or cocktails of lipid antigen(s) for the purpose of inducing immune tolerance (Example 3, below). Lipid arrays enable multiplex characterization of anti-lipid antibody specificity and can thereby be applied to determine the specificity of the autoimmune response in a variety of autoimmune diseases.

Methods

Lipids. Lipids were obtained from Matreya, Avanti Polar Lipids, Calbiochem, Sigma Chemicals, Biodesign International, and Accurate Chemical (see Table 1 for complete list) and dissolved in mixtures of chloroform, methanol, and water to a final concentration of 1 mg/ml, except for gangliosides which were diluted to 0.1 mg/ml and LPS and teichoic acid which were diluted to 0.01 mg/ml.

| LIPID | VENDOR |
|---|---|
| Disialoganglioside-GD1A | Matreya |
| Disialoganglioside-GD1B | Matreya |
| Disialoganglioside-GD2 | Biodesign International |
| Trisialoganglioside-GT1B | Matreya |
| Cardiolipin | Sigma |
| Cholesterol | Sigma |
| Squalene | Sigma |
| Asialoganglioside-GM2 | Biodesign International |
| Brain phosphatidylinositol-4 phosphate | Avanti Polar lipids |
| Brain polar lipid extract | Avanti Polar lipids |
| Brain sulfatide | Avanti Polar lipids |
| Brain total lipid extract | Avanti Polar lipids |
| Brain ceramides | Avanti Polar lipids |
| Brain D-erythrosphingosine | Avanti Polar lipids |
| Brain lysophosphatidylethanolamine | Avanti Polar lipids |
| Brain L-α-lysophosphatidylserine | Avanti Polar lipids |
| Brain L-α-phosphatidylcholine | Avanti Polar lipids |
| Brain L-α-phosphatidylserine | Avanti Polar lipids |
| Brain L-α-phosphatidyl-ethanolamine | Avanti Polar lipids |
| Brain sphingomyelin | Avanti Polar lipids |
| Total cerebroside | Avanti Polar lipids |
| Purified mixed gangliosides | Matreya |
| Ganglioside-GM4 | Calbiochem |
| Lactosyl ceramide | Calbiochem |
| Monosialoganglioside-GM1 | Matreya |
| Monosialoganglioside-GM2 | Matreya |
| Disialoganglioside-GD3 | Matreya |
| Tetrasialoganglioside-GQ1B | Accurate Chemical |
| Monosialoganglioside-GM3 | Matreya |
| Gangliotetraosyl ceramide asialo-GM1 | Matreya |
| Lipoteichoic acid from S. aureus | Sigma |
| Trehalose 6,6'-dimycolate from M. tuberculosis | Sigma |
| LPS from E. coli | Sigma |
| LPS from P. aeruginosa | Sigma |
| Mycolic acid from M. tuberculosis | Sigma |
| Lipoteichoic acid from B. subtilis | Sigma |
| LPS from S. typhimurium | Sigma |
| Lyso-GM1 | Matreya |
| Fucosyl-GM1 | Matreya |
| Lipoteichoic acid from S. pyogenes | Sigma |
| 1-Palmitoyl-2-Azelaoyl-sn-Glycero-3-Phosphocholine | Avanti Polar Lipids |
| 1-Palmitoyl-2-Glutaroyl-sn-Glycero-3-Phosphocholine | Avanti Polar Lipids |
| 1-Palmitoyl-2-(9'-oxo-Nonanoyl)-sn-Glycero-3-Phosphocholine | Avanti Polar Lipids |
| 5α-cholest-8(14)-ene-3β,15β,-diol | Avanti Polar Lipids |
| 3β-hydroxy-5α-cholest-8(14)-en-15-one | Avanti Polar Lipids |
| 3β-hydroxy-5α-cholestan-15-one | Avanti Polar Lipids |
| 5α-cholestane-3β,15α-diol | Avanti Polar Lipids |

Antibodies. Antibodies against GM1, GM2, asialo-GM1, GD3 and GM4 were purchased from Matreya and Calbiochem. Anti-cardiolipin lupus patient serum was purchased from Immunovision and Louisville APL Diagnostics. Anti-sulfatide and anti-cerebroside antibodies were obtained from the O4 and O1 hybridomas. Purified O4 antibody was also purchased from R&D Systems. IgM isotype control was purchased from Chemicon International.

Lipid array production. A Camag Automatic TLC Sampler 4 (ATS4) robot was adapted to print lipids in ordered arrays on PVDF membranes affixed to the surface of microscope slides using double-sided Scotch tape (3M). The ATS4 sprays 200 nL containing 10 to 100 pmol of lipids solubilized in chloroform/methanol/water mixtures under nitrogen gas to form individual features. At our current printing density, the ATS4 can print arrays containing up to 200 individual features. Twelve slides are printed in each "print run". Printed membranes are stored dry and retained reactivity for several months.

Probing lipid arrays. Arrays were blocked overnight in 4° C. with 1% fatty acid free bovine serum albumin (BSA; Sigma) in phosphate buffered saline (PBS; Gibco BRL). Arrays were then probed with 1/10 dilutions of CSF, or 1/200 dilutions of sera for 2 hours at 4° C. After washing with blocking solution, a secondary antibody (anti-human IgG+ IgM, Jackson Immunoresearch; anti-human IgG, Jackson Immunoresearch; anti-rabbit IgG, Amersham; or anti-mouse IgG, Amersham) conjugated to horseradish peroxidase (HRP) was added in blocking solution, and bound secondary antibodies visualized using chemiluminescence (ECL Plus, Amersham) and autoradiography.

Lipid ELISA. Costar enzyme immunoassay plates were coated with gangliosides (1 µg/well) and cardiolipin (2 µg/well), blocked with Assay Diluent (Pharmingen), and primary antibody binding detected with HRP-conjugated anti-human IgG or anti-rabbit IgG.

Example 2

Use of Anti-Lipid Antibodies for Diagnosis and Assessing Prognosis of Autoimmune Demyelinating Disease MS patients possess antibodies against multiple myelin lipids. Lipid arrays were applied to profile anti-lipid antibody responses in CSF derived from 16 MS patients (8 relapsing remitting (RR); 8 secondary progressive (SP)) and 11 other neurological disease control patients. Lipid array reactivity was quantified and a statistical tool known as Significance Analysis of Microarrays (SAM; Tusher et al. (2001) *Proc Natl Acad Sci USA* 98, 5116-21) was applied to identify lipids with statistically-significant differences in array reactivity between MS and control samples. SAM-identified lipid features were ordered using a hierarchical cluster algorithm, and cluster results displayed as a heatmap using TreeView software (Eisen et al. (1998) *Proc Natl Acad Sci USA* 95, 14863-8). The MS patient samples clustered, and demonstrated strong and statistically increased reactivity to lipids including sulfatide, 3β-hydroxy-5α-cholestan-15-one (an oxidized form of cholesterol), two separate forms of oxidized phosphatidylcholine, phosphatidyl-ethanolamine, lysophosphatidyl-ethanolamine, and sphingomyelin, and demonstrated weaker reactivity to bacterial LPS and the ganglioside asialo-GM1 (FIG. 2a). One OND patient (4117) with spinal stenosis, which is not an inflammatory disorder, but is due to an anatomical narrowing of the spinal canal, clustered among the MS patients.

Thus, detection of increased antibody reactivity against lipids including sulfatide and sphingomyelin; oxidized lipids including 3β-hydroxy-5α-cholestan-15-one, and 1-palmitoyl-2-(9'-oxo-nonanoyl)-sn-glycero-3-phosphocholine; and against microbial lipids including LPS provides diagnostic utility for MS. Further, such antibody reactivities distinguish MS from other neurologic diseases.

In inflamed MS brain plaques, there are reactive oxygen species such as nitric oxide which could oxidize lipids to create neoantigens that become targets of an autoimmune response. In fact, the brain and myelin lipid compositions differ between MS patients and healthy people. FIG. 2a demonstrates that MS patients have statistically increased antibody reactivity against oxidized lipids, specifically cholesterol and PGPC, as compared to other neurologic disease controls, and thus detection of antibodies against oxidized lipids provides utility for the diagnosis of MS.

When we applied SAM to statistically compare only patients with secondary progressive (SP) MS with the OND controls, SAM identified increased reactivity to two gangliosides, GM1 and asialo-GM1, in the SP MS patients (FIG. 2b). Thus, SP MS patients exhibit statistically increased reactivity to the ganglioside GM1 (FIG. 2b). Gangliosides are quantitatively enriched in the outer leaflet of the plasma membranes of neuronal cells, and the anti-ganglioside antibodies observed in these patients may facilitate the destruction of neurons which is associated with SP MS. Our data demonstrate that detection of anti-asialo-GM1 and/or other anti-ganglioside antibodies could be used to differentiate SP MS from RR MS and thereby provide the treating physician with prognostic information. Thus, detection of anti-asialo-GM1 and other anti-ganglioside antibodies could predict that an individual patient is likely to develop secondary progressive MS, a more severe and debilitating form of this disease. Such prognostic information would guide the physician to treat the MS patient predicted to progress to SP MS with more aggressive therapy such as with beta interferons, copaxone, anti-VLA4 (Tysabri (Natalizumab) produced by Biogen-IDEC), and/or other small molecule and biological drugs that provide efficacy preventing progression to and treating SP MS. In contrast, if the individual with MS lacked such antibodies, the patient would be treated with a regimen more suitable for the treatment of RR MS, which is currently generally a less aggressive therapeutic regimen (such as beta interferons or copaxone alone).

Figure 2:
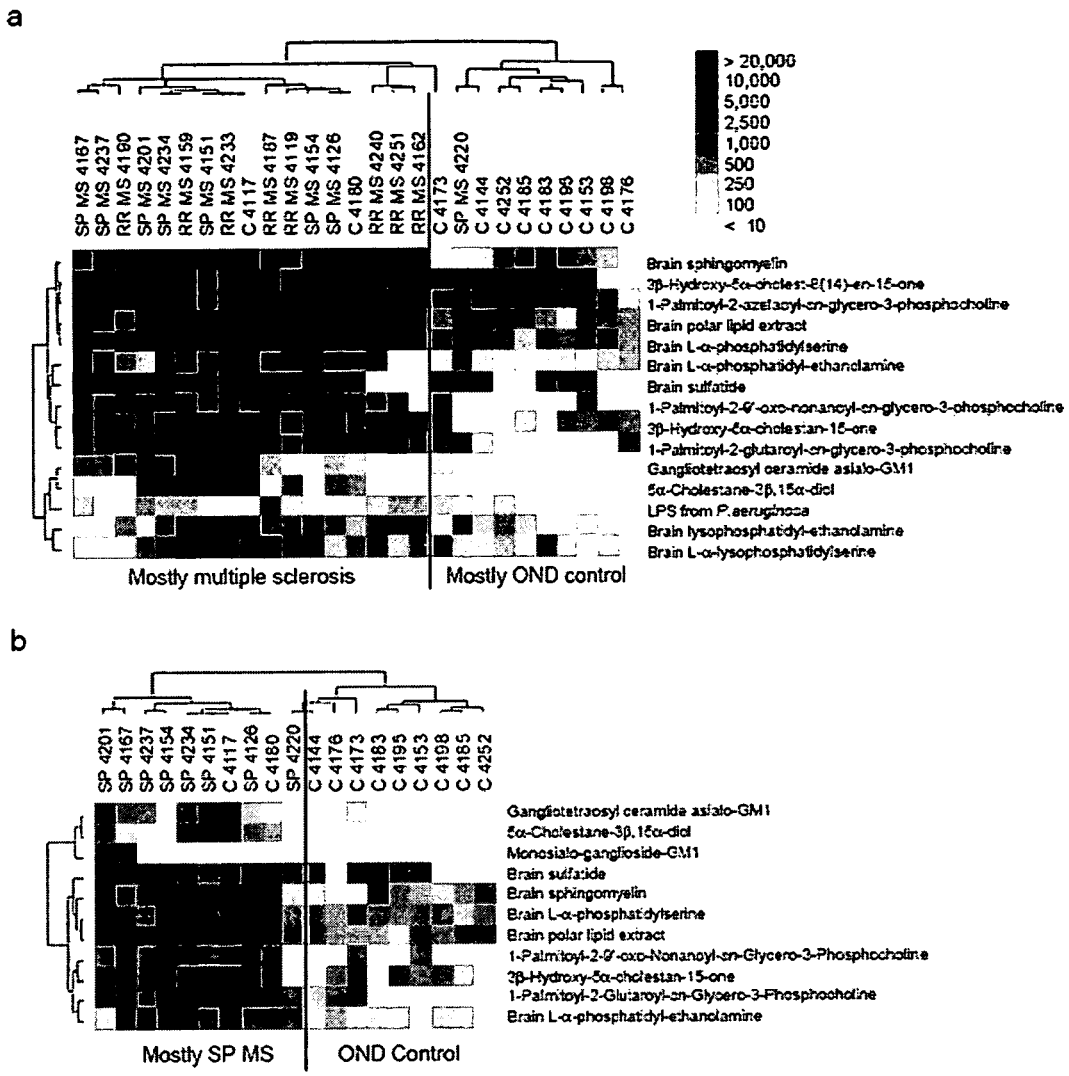
FIG. 2a-2b. MS patients possess increased anti-lipid antibodies. (a) Lipid array profiling of antibody reactivity in 16 MS and 11 other neurological disease (OND) control CSF samples. Significance Analysis of Microarrays (SAM) was applied to identify lipid antigen features with statistical differences in antibody reactivity in MS samples as compared to OND samples (listed to the right of the heatmap; all anti-lipid antibody reactivities identified with statistically increased in MS as compared to controls). A hierarchical cluster algorithm was used to group patients (labeled along the top of the heatmap) and SAM-identified lipid antigens (labeled to the right of the heatmap) based on similarities in their array reactivity patterns. Dendrograms depicting the cluster relationships between patients are displayed above, and between lipid antigens to the left. After clustering, labels were added at the base of the heatmap to indicate the general location of the MS and OND patient clusters. (b) SP MS patients possess increased anti-ganglioside antibodies compared to OND controls. Analysis was performed as described in (a).
Figure 3:
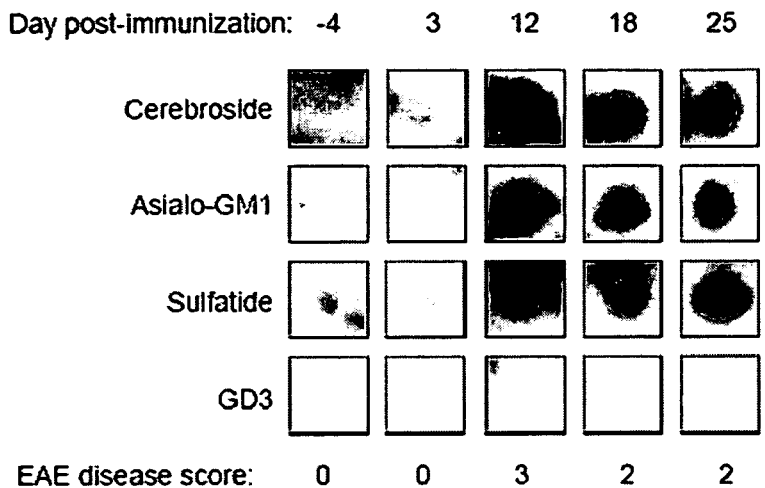
FIG. 3a-3b. Mice with EAE have increased anti-lipid antibodies. (a) Serial serum samples derived from SJL mice induced for EAE with $PLP_{139-151}$, emulsified in CFA were analyzed on lipid microarrays. Antigen features representing the cerebroside, asialo-GM1 and sulfatide lipids from individual arrays were cut and pasted into columns to facilitate visual analysis. Ganglioside GD3 features provide an example of a lipid with no increase in anti-lipid antibodies over EAE disease course. (b) Pre-induction (day-1, naïve) and acute EAE (day 20) serum samples from C57BL/6 mice induced for EAE with $MOG_{35-55}$ were analyzed on lipid arrays. Statistical analysis and display of array data was performed as described in FIG. 2. The list of lipids determined to have statistical differences in reactivity in samples derived from mice with acute EAE as compared to naive mice is displayed to the, right of the heatmap (all anti-lipid reactivities identified were statistically increased in acute EAE mice as compared to naive mice).
Figure 3:
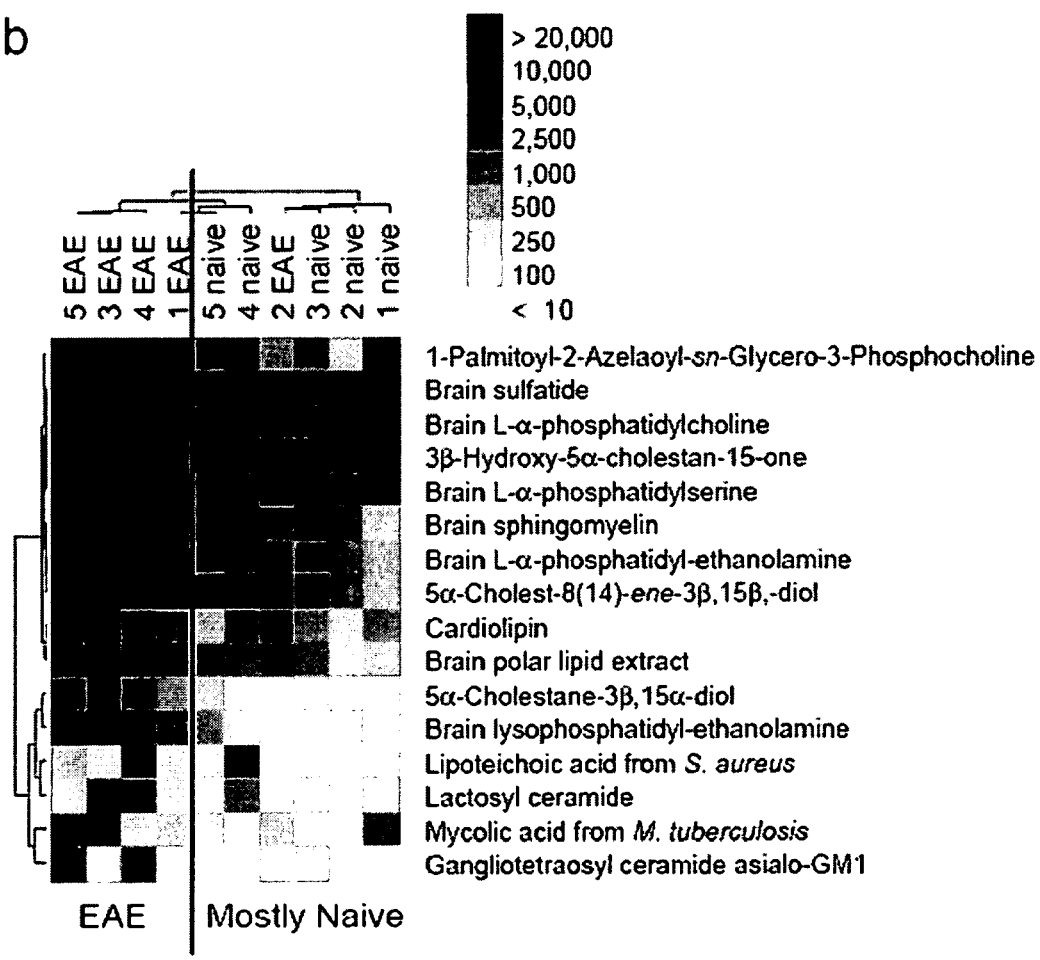

Mice with acute EAE possess anti-lipid antibodies. Based on our observations of anti-lipid autoantibodies in human MS (FIG. 2), it was next determined if autoantibodies directed against sulfatide and other lipids were present in mice with EAE. Lipids arrays were probed with sera derived from SJL and C57BL/6 (B6) mice induced for EAE with one of two non-lipidated myelin peptides, either $PLP_{139-151}$ or $MOG_{35-55}$, respectively, emulsified in complete Freund's adjuvant (CFA). Lipid arrays identified autoantibodies directed against sulfatide, asialo-GM1, cerebroside and other lipids in serum derived from mice with EAE (FIG. 3). In SJL mice, anti-lipid antibody reactivities were very low pre-induction (day-4) and immediately following EAE disease induction (day 3), while significant reactivity was detected and persisted following development of paralysis that characterizes clinical EAE (FIG. 3a). We also observed increased antibodies binding brain polar lipid extract, oxidized lipids, and sulfatide in samples from B6 mice with established EAE as compared to pre-induction samples (FIG. 3b). These data suggest that autoreactive B cell responses in EAE, in addition to expanding to target additional polypeptide epitopes, also undergo inter-molecular epitope spreading to target lipid components of the myelin sheath. Compilation of results from lipid array analyses identified a panel of lipids targeted by antibodies in both murine EAE and human MS, including sulfatide, oxidized phosphocholine, oxidized cholesterol, sphingomyelin and asialo-GM1 (FIGS. 2 and 3).

These data demonstrate that multiplex analysis of anti-lipid antibody profiles reveals lipid-specific antibody profiles with diagnostic and prognostic utility for human MS, and that murine EAE develops similar autoantibodies further validating it as a relevant model for human MS. As known to those skilled in the art, such anti-lipid antibodies can also be detected by conventional immunoassays such as enzyme-linked immunbsorbent assays (ELISAs), fluorescent immunoassays, bead-based immunoassays, and other immunoassay platforms.

The invention provides a method for the identification of patients likely to develop a more severe form of disease, enabling selection of more aggressive small molecule and protein biological therapy based on a patient's antibody specificity profile. In another embodiment, antigen-specific therapies can be selected based on the antibody-specificity profile. Individualized cocktails of antigen specific treatments can be formulated based on the patient's specificity profile. In yet another embodiment, identification of a consensus of common antibody specificity profiles between patients with the same immune disorder provides for formulation of a generic antigen-specific therapy to treat patients with that disease.

In another aspect of the invention, lipid-specific antibody profiles are useful for monitoring therapeutic response in a patient receiving treatment for immune-related disorders. Therapeutic responses are assessed based on alterations in the antibody specificity profile including changes in antibody targets (i.e. the specificity of anti-lipid antibodies present in the patient), changes in antibody titers, changes in antibody isotypes, and changes in large-scale patterns of antibody recognition. In another embodiment, antibody specificity profiles can be utilized to predict adverse outcomes in individual patients, thereby enabling selection of alternative therapies.

Methods

Lipid array production and probing. Lipid array were produced and probed as described in Example 1, above.

Patient samples. All human samples were collected and utilized under Institutional Review Board approved protocols and with informed consent. All MS patients except 4154 were undergoing a relapse at the time of lumbar puncture. All MS patients except 4251 possessed oligoclonal bands in their CSF, while all OND controls were negative. OND controls included patients with motor neuron disease (4252), vascular leukoencephalopathy (4173), spinal stenosis (4117), clipped cerebral aneurysm with functional neurological symptoms (4185), a patient undergoing breast implant removal who was having functional neurological symptoms (4198), and other patients having a functional neurological symptom where MS was ruled out.

Analysis of lipid array data. GenePix Pro 5.0 software (Axon Instruments) was used to extract the net median pixel intensities for individual features from the digital images produced by scanning array autoradiographs. Median net digital chemiluminescence units were generated from the median values from 2-4 identical lipid antigen features on each array. The Significance Analysis of Microarrays (SAM) algorithm was applied to identify lipids with statistically-significant differences in array reactivity between groups of human patients or mice. SAM results were arranged into relationships using Cluster software.

EAE induction. For induction of EAE in C57BL/6 mice (Jackson Mice), 8-10 week old female mice were induced by subcutaneous immunization with 100 μg of $MOG_{35-55}$ emulsified in complete Freund's adjuvant (CFA; Difco Laboratories), accompanied by 300 ng of pertussis toxin (Life Technologies) intraperitoneally on days 0 and 2. For induction of EAE in SJL mice (Jackson Mice), 8- to 10-wk-old female animals were immunized subcutaneously with 100 μg of $PLP_{139-151}$ emulsified in CFA. Animal experiments were approved by and performed in compliance with the guidelines of the Institutional Animal Care and Use Committee.

Example 3

Treatment of Multiple Sclerosis with Lipid Therapies

Figure 4:
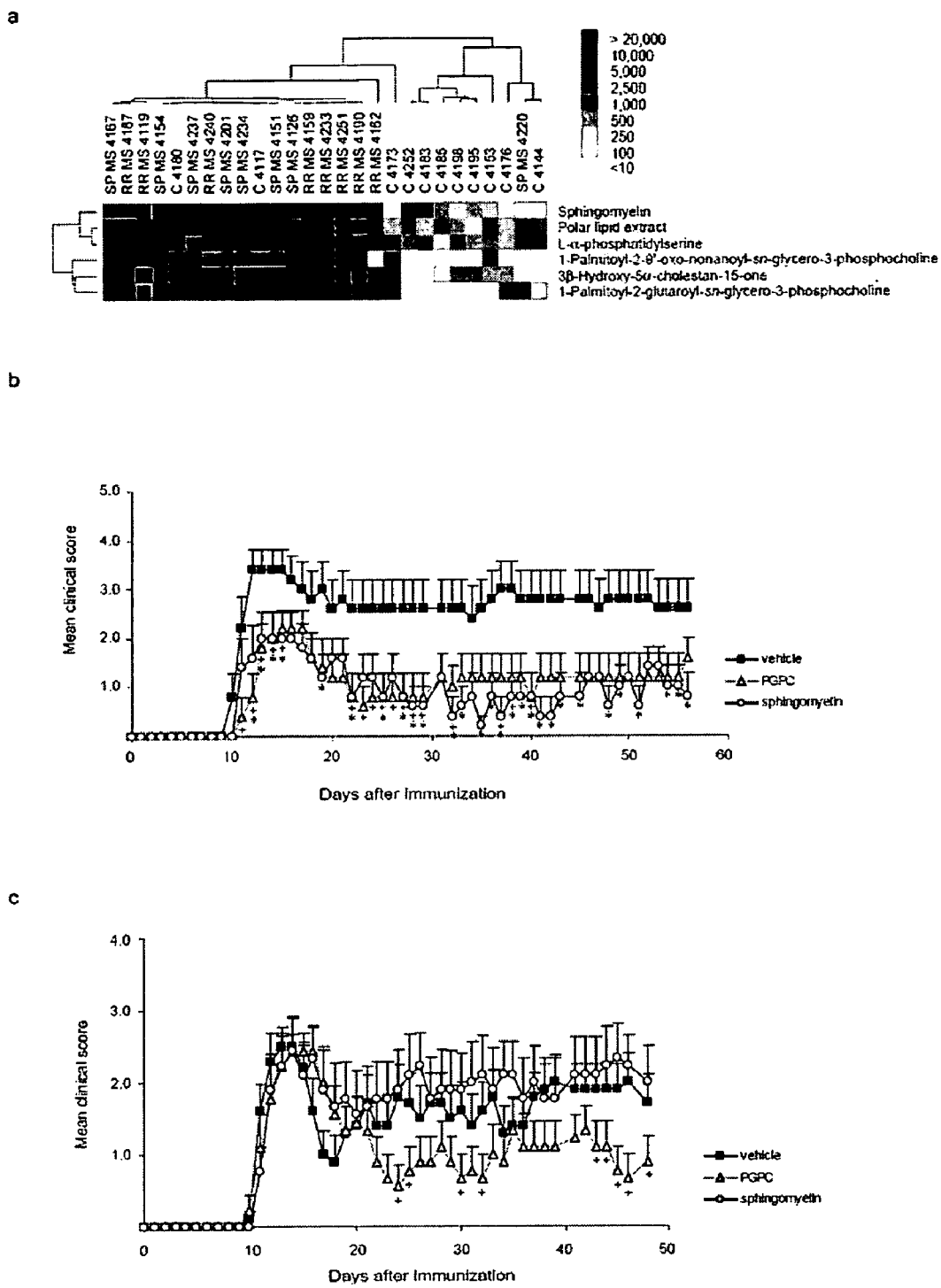
FIG. 4a-4c. Array identified lipids ameliorate EAE. (a) Lipid array profiling of antibody reactivity in MS and other neurological disease (OND) control CSF samples. Lipid hits with the lowest q value (q=0.039) and a SAM score of >3.0, listed to the right of the heatmap, were clustered based on their reactivity profiles (all anti-lipid antibody reactivities identified exhibited statistically increased reactivity in MS as compared to OND controls). (b) PGPC and sphingomyelin administration ameliorates EAE. Six micrograms PGPC or sphingomyelin was administered on days 0, 4, and 7 post-immunization. On day 0 lipids were mixed with the peptide/CFA emulsion and injected subcutaneously. On days 4 and 7, lipids were solubilized in vehicle 0.05% Tween-20 in PBS and injected into the intraperitoneal cavity. Each point represents the mean+s.e.m. Statistically significant points comparing vehicle control (n=5, black squares) and PGPC (n=5, gray triangles) groups are denoted by +p<0.05 (non-parametric Mann-Whitney test). Statistically significant points comparing vehicle control (n=5, black squares) and sphingomyelin (n=5, white circles) groups are denoted by (p<0.05 by Mann-Whitney). (c) Upon presenting with clinical signs of EAE, mice were treated with 100 µg PGPC (gray triangles, n=9) or sphingomyelin (white circles, n=9), or vehicle alone (black squares, n=10) for a total of five intravenous injections. Each point represents the mean+s.e.m. Statistically significant points comparing PGPC treatment to vehicle control and sphingomyelin groups are denoted by +p<0.05 (Mann-Whitney).

To narrow the list of lipids to study as tolerizing agents, we performed analysis of our lipid array datasets (FIG. 2a) using more stringent statistical cutoffs. We applied the Significance Analysis of Microarrays (SAM) algorithm to identify lipids with statistically-significant differences in our lipid array-determined anti-lipid antibody reactivity between 16 individuals with MS and 11 controls with other neurological diseases. SAM-identified anti-lipid antibody reactivities were ordered using a hierarchical cluster algorithm, and most individuals with MS clustered together based on similarities in their anti-lipid antibody reactivity profiles. Lipid "hits" with the lowest false discovery rate (false discovery rate (q)=0.039) that exhibited the greatest differences between the groups (SAM score of >3.0) were used for the clustering. This analysis reduced the "hit list", of lipids to a group of six, including two related derivatives of phosphocholine, 1-palmitoyl-2-9'-oxo-nonanoyl-sn-glycero-3-phosphocholine and PGPC, as well as sphingomyelin, polar lipid extract, and L-α-phosphatidylserine (FIG. 4a) (all of these "lipid hits" demonstrated statistically increased anti-lipid antibody reactivity in MS as compared to OND control samples).

PGPC and sphingomyelin were chosen for further in vivo analyses. In brain lesions, inflammation leads to an increase in nitric oxide which can oxidize lipid components of the brain. Phosphatidyl-choline makes up 30.1% and 15.0% of the lipids in the gray and white matter of an adult human brain, respectively. PGPC and other oxidized components of phosphatidyl-choline were first identified in atherosclerosis lesions. Sphingomyelin composes 6.9% and 7.7% of the lipids in the gray and white matter of an adult human brain, respectively.

Prevention of murine multiple sclerosis (EAE). Six micrograms of PGPC or sphingomyelin was emulsified with 100 μg $PLP_{139-151}$ in complete Freund's adjuvant (CFA) and administered subcutaneously to SJL/J mice. At days 4 and 7 post-immunization, 6 μg lipid or vehicle was administered intraperitoneally. PGPC and sphingomyelin both statistically reduced the severity of EAE throughout the disease course (FIG. 4b).

Treatment of established murine multiple sclerosis (EAE). To further examine the ability of PGPC and sphingomyelin to ameliorate established murine multiple sclerosis, we administered these lipids to mice with ongoing EAE. 100 μg of lipid was injected intravenously into the tail of mice upon development of tail or hind limb paralysis and on days 3, 6, 12 and 18 following development of clinical EAE with paralysis, for a total of five separate injections over the disease course in an analogous regimen to that previously reported for peptide treatment of EAE. PGPC reduced the severity of paralysis and was thus able to treat established EAE (FIG. 4c).

Thus, administration of PGPC and sphingomyelin, two lipids identified as targets of the anti-lipid antibody response in both murine (EAE) and human MS, provide therapeutic benefit in the mouse model of multiple sclerosis (EAE) and thus are anticipated to provide therapeutic benefit in human MS.

Example 4

Characterization of Candidate Lipid Tolerogens

Lipid array profiling of autoantibody specificities present in individual patients is used to determine the specific antigens against which an individual patient's autoimmune response is directed. For example, as described above, lipid arrays were used to profile anti-lipid antibody responses in CSF derived from 16 MS patients and 11 other neurological disease control patients. The MS patient samples clustered, and demonstrated statistically increased reactivity to lipids including sulfatide, 3β-hydroxy-5α-cholestan-15-one (an oxidized form of cholesterol), two separate forms of oxidized phosphatidylcholine, phosphatidyl-ethanolamine, lysophosphatidyl-ethanolamine, and sphingomyelin, and demonstrated weaker reactivity to bacterial LPS and the ganglioside asialo-GM1 (FIGS. 2a, 4a). Many of these same anti-lipid antibody specificities were present in mice with EAE, further validating its use as a relevant model for human MS. We then tested these lipids in mice to see if they modulated EAE disease course, and found that sphingomyelin and PGPC treat murine MS while sulfatide exacerbated murine MS.

The following provides methods to differentiate disease protective (tolerizing) from disease exacerbating lipids, and thereby identify candidate lipids that could be used as efficacious therapeutic agents for the treatment of human MS, other autoimmune demyelinating and other autoimmune diseases. These methods are based on testing the effects of candidate therapeutic lipids in: (i) the murine model for MS, EAE, and (ii) on human peripheral blood cells. If the candidate therapeutic lipid: (i) prevents and/or treats EAE, (ii) reduces autoreactive T and/or B cell responses in EAE and in vitro and/or human peripheral blood mononuclear cells in vitro, and (iii) induces protective (IL-4, IL-10) and reduces pathogenic (TNFa, IFNgamma, IL-23) cytokine responses in cells derived from EAE and/or human peripheral blood; then the lipid is likely to provide therapeutic benefit in human MS. In contrast, if the candidate lipid: (i) exacerbates or is unable to prevent/treat EAE, (ii) increases autoreactive T and/or B cell responses in EAE and in vitro and/or human peripheral blood cells in vitro, or (iii) induces pathogenic (TNFalpha, IFNgamma, IL-23) cytokine responses in cells derived from EAE or human peripheral blood; then the lipid is not a good candidate therapeutic and could exacerbated human MS.

Figure 5:
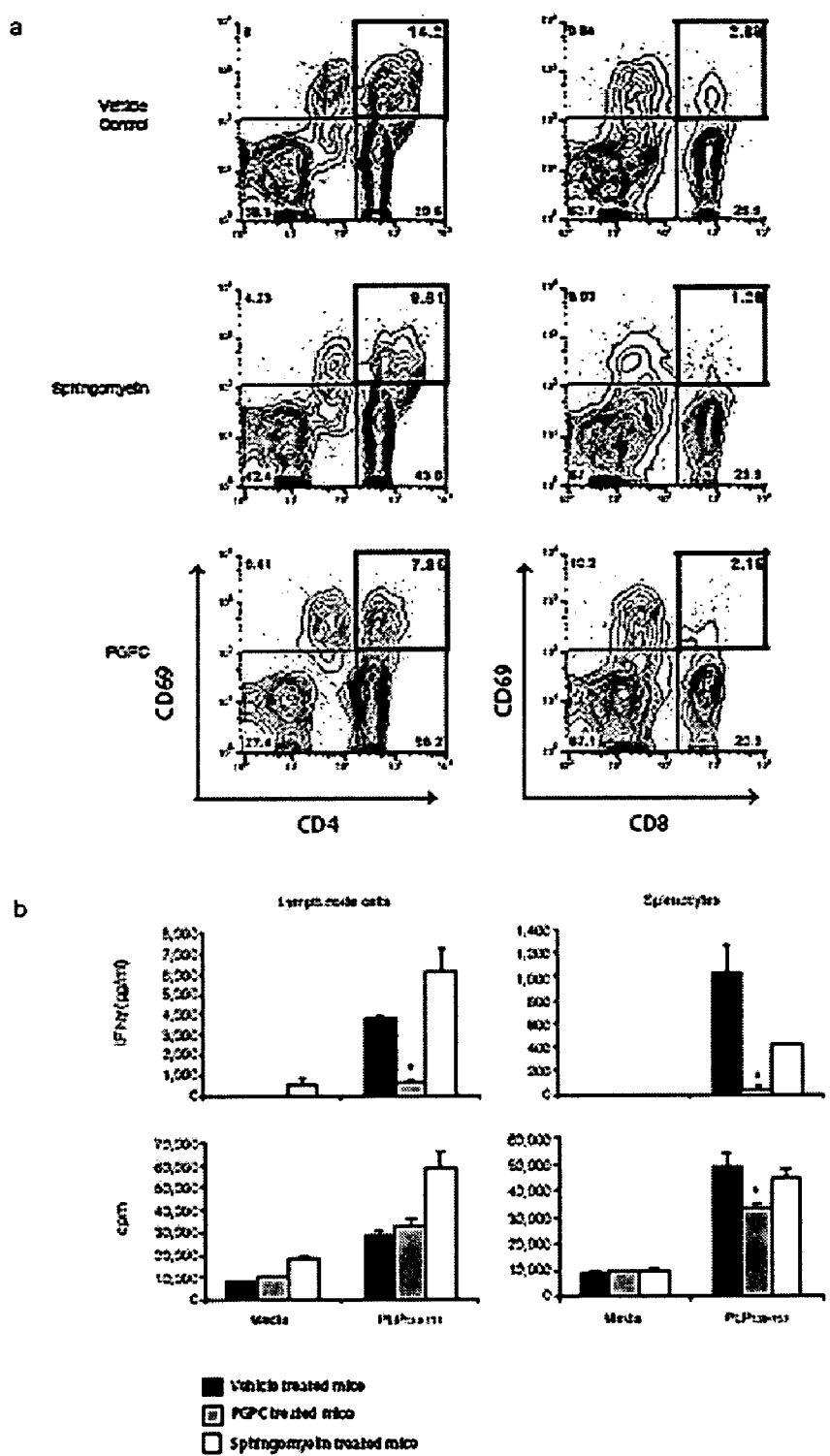
FIG. 5a-5b. PGPC treatment lowers IFNgamma secretion and early activation marker expression in response to the encephalitogenic antigen. (a) CD69 expression on CD4+ and CD8+PI− lymphocytes (live cells) after 4 days in culture with 10 μg/ml PLP$_{139-151}$. The ratio of CD69+CD4+:CD69−CD4+ is 14.2%:39.6% for lymph node cells from vehicle-treated mice, 9.6%:43.8% for cells from sphingomyelin-treated mice, and 7.96%:55.2% for cells from PGPC-treated mice. CD69+ CD4+ cells and CD69+ CD8+ cells are boxed in red and percentages of cells in each quadrant are displayed. (b) Proliferation and cytokine assays of lymph node cells and splenocytes isolated from vehicle, PGPC, and sphingomyelin-treated mice in FIG. 4c. Lymph node cells and splenocytes from PGPC-treated mice (gray bars) secreted lower levels of IFNγ in response to PLP$_{139-151}$, p=0.0041 and p=0.049, respectively (Student's t test). PGPC-treated mouse splenocytes also displayed slightly lower proliferation, p=0.036 (Student's t test), in response to PLP$_{139-151}$.

Demonstration that PGPC and sphingomyein are therapeutic (tolerance-promoting) lipids). LN cells from PCPG and sphingomyelin injected mice showed decreased IFNγ levels when stimulated with the PLP peptide used to induce EAE. FIG. 5B. A similar trend was seen in TNF production by splenocytes from these lipid-treated mice. A reduction in these pro-inflammatory cytokines, by these array-identified lipids, likely plays a role in the disease amelioration. FIG. 5C.

Mice were sacrificed 48 days after disease induction and their spleens and lymph nodes (LN) harvested for analyses of expression of activation markers on subsets of T cells, measurements of secreted cytokines, and levels of T cell proliferation. Isolated cells were restimulated with the encephalitogenic antigen $PLP_{139-151}$ and analyzed by flow cytometry. Dead cells (identified based on staining with propidium iodide) were eliminated from the analyses, and cells double stained with CD4-FITC or CD8-FITC and CD69-PE are presented (FIG. 5a). Cells isolated from PGPC treated mice showed a marked reduction in the expression of the early activation marker CD69 on $CD4^+$ T cells. Specifically, the cells isolated from vehicle treated mice were 39.6% $CD4^+CD69^-$ and 14.2% $CD4^+CD69^+$, whereas cells from PGPC treated mice were 55.2% $CD4^+CD69^-$ and 7.96% $CD4^+CD69^+$. $CD4^+$ T cells derived from sphingomyelin treated mice exhibit an intermediate level of CD69 expression, 43.8% $CD4^+CD69^-$ and 9.61% $CD4^+CD69^+$, as compared to those isolated from mice treated with vehicle and PGPC (FIG. 5a). Lymph node cells and splenocytes isolated from PGPC treated mice secreted less IFNgamma upon stimulation with the encephalitogenic $PLP_{139\text{-}151}$ peptide compared to controls (p=0.0041, p=0.049, Student's t test) (FIG. 5b). $^3$H-thymidine incorporation was also reduced in $PLP_{139\text{-}151}$ stimulated splenocytes from PGPC treated mice (p=0.036) (FIG. 5b).

Figure 6:
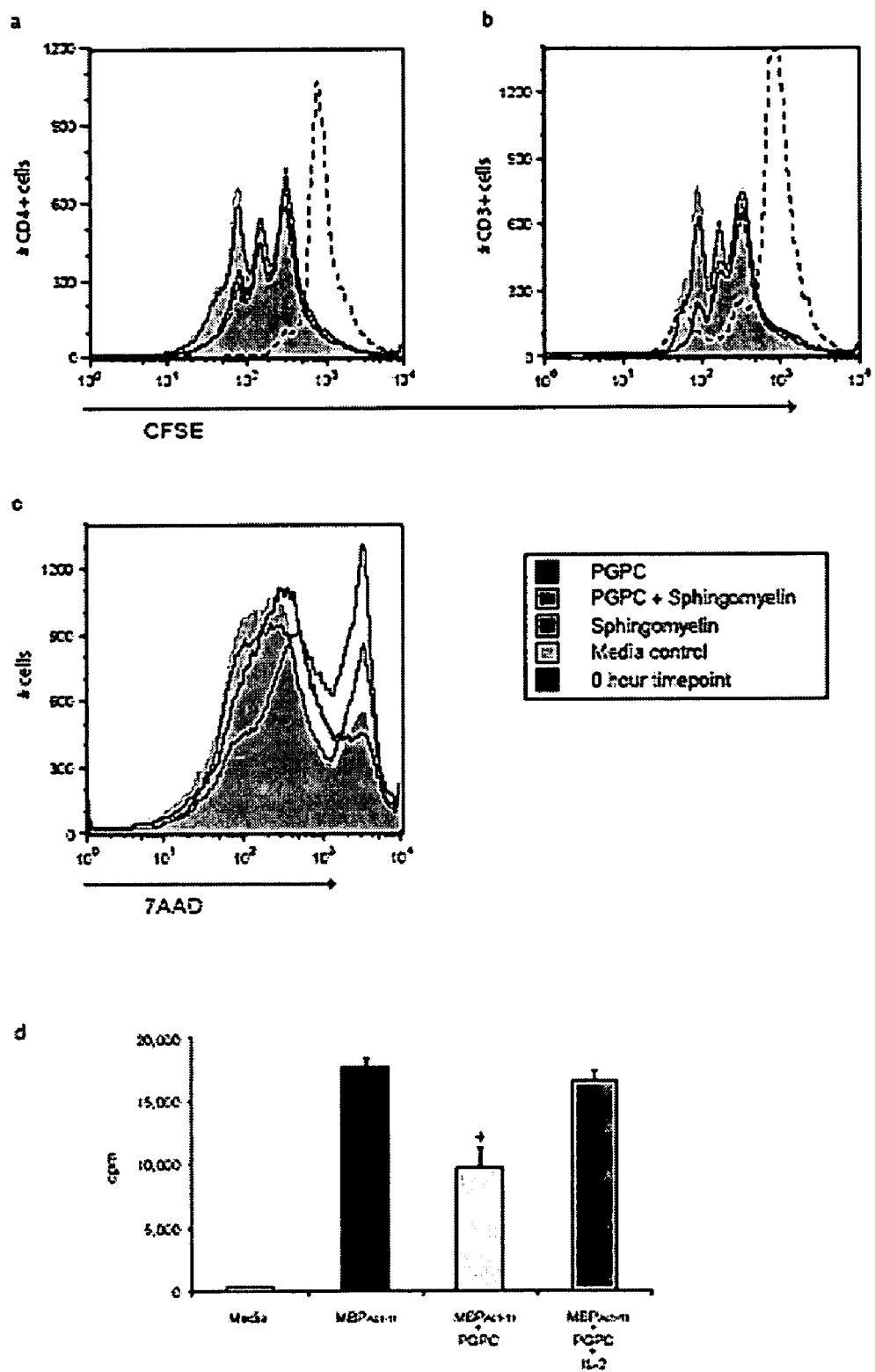
FIG. 6a-6d. PGPC slows the rate of T cell proliferation. (a-b) CFSE stained CD4+ LN cells (a) or CD3+ LN cells (b) from TCR Tg mice[33], 48 hours after culturing with 5 μg/ml MBP$_{Ac1-11}$ and 75 μM sphingomyelin (line parallels gray shaded area in a and b); 75 μM PGPC or 75 μM PGPC+75 μM sphingomyelin (PGPC and PGPC+sphingomyelin lines parallel each other, and are shifted moderately to the right of the gray shaded area [demonstrating reduced cell divisions]), or media alone (gray shaded area). The 0 hour time point is shown as the high peak with the black dashed line. (c) 7AAD stained cells from TCR Tg mice[33], 48 hours after incubation with 5 μg/ml MBP$_{Ac1-11}$ with or without lipid. All groups generally parallel the media control (media control represented by the gray shaded area), demonstrating that PGPC, PGPC+sphingomyelin, and sphingomyelin treatment are not inducing cell death. (d) LN cells stimulated with 1 μg/ml MBP$_{AC1-11}$, 30 μg/ml PGPC, with or without 50 U/ml IL-2 are depicted. PGPC reduced cell proliferation in response to MBP$_{Ac1-11}$ (p=0.0099, Student's t test), and IL-2 reversed this effect (p=0.024, Student's t test).

To determine if sphingomyelin or PGPC influences antigen specific T cell proliferation, we examined their ability to slow T cell proliferation using 5 µg/ml $MBP_{Ac1\text{-}11}$ stimulation of TCR Tg LN cells. Harvested LN cells were loaded with carboxyfluorescein diacetate succinimidyl ester (CFSE) using the CellTrace™ CFSE Cell Proliferation Kit (Molecular Probes) and then incubated with 75 µM sphingomyelin, 75 µM PGPC, a combination of 75 µM PGPC and 75 µM sphingomyelin, or media alone. At 48 hours, cultures containing PGPC, but not sphingomyelin, exhibited slowed T cell proliferation in response to $MBP_{AC1\text{-}11}$. Both the $CD3^+$ and $CD4^+$ T cells populations displayed a similar result (FIG. 6a-b). Our data demonstrate that PGPC decreases antigen-specific T cell proliferation.

To determine if the PGPC-mediated reduction in the proliferation rate of $MBP_{AC1\text{-}11}$ stimulated T cells was due to cell death, we examined 7AAD uptake to identify dead cells at the 48 hour time point (FIG. 6c). At this time point, cultures containing sphingomyelin or combination PGPC+sphingomyelin exhibited increased cell death (peak at $10^3$-$10^4$ 7AAD-positive cells, FIG. 6c), yet the CFSE staining profile of cells in cultures containing sphingomyelin mirrored that of the control and the PGPC+sphingomyelin combination mirrored that of cultures containing PGPC alone (FIG. 6a-b). Therefore, PGPC reduces proliferation rates of antigen-specific T cells and this effect is not due to cell death. To confirm our CFSE results, we performed proliferation assays based on $^3$H-thymidine incorporation and demonstrated that addition of PGPC resulted in statistically significant reductions in $MBP_{Ac1\text{-}11}$-specific T cell proliferation (p=0.0099, Student's t test) (FIG. 6d). This effect could be reversed by the addition of 50 U/ml IL-2 (p=0.024, Student's t test) (FIG. 6d), consistent with IL-2 mediated rescue of the T cells from an anergic state.

Both PGPC and sphingomyelin were identified in our lipid microarray studies as targets of antibodies in individuals with MS compared to other neurological disease controls (FIG. 4a). Both sphingomyelin and PGPC ameliorate EAE when co-delivered with the encephalitogenic PLP peptide in the emulsion. However, only PGPC treats ongoing disease as well as reduces T cell proliferation rates. It is possible that the effects of the co-delivered sphingomyelin are attributable to apoptosis of self-reactive cells as sphingomyelin is a component of the ceramide-induced apoptosis pathway. This pathway leads to apoptosis in many cell types, and our unpublished data along with other reports found components of this pathway to promote apoptosis in autoreactive T cells.

This discovery and therapeutic approach varies considerably from the approach of Miyamoto and colleagues (Miyamoto et al, Nature 413:5314, 2001). They showed that a synthetic variant of the sponge-derived lipid alpha galactosylceramide, also known to be a ligand for NK T cells, could be used to treat EAE. This synthetic lipid enhanced Th2 responses by stimulating NK T cells, and has not been shown to be a target of the autoimmune response in human MS.

Figure 8:
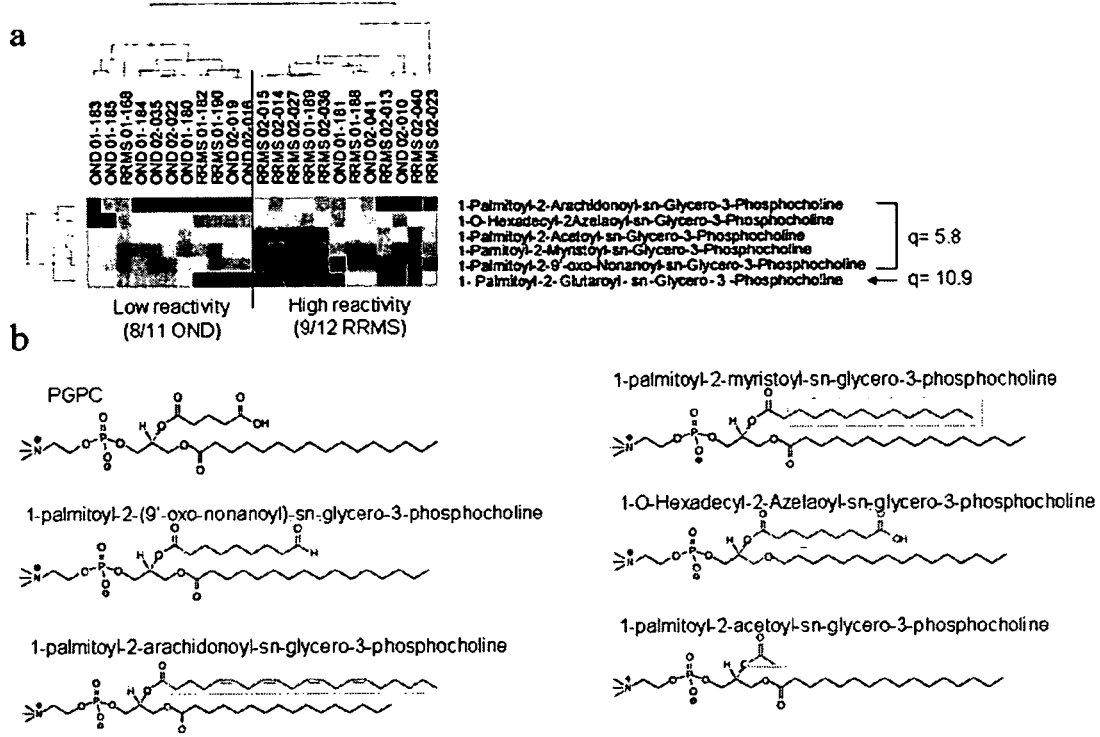
FIG. 8. Characterization of autoantibody reactivity against PGPC-related glycerophosphocholine lipids in MS. (a) Lipid arrays were used to profile lipid directed antibodies in the CSF of patients characterized with either relapse-remitting MS (RRMS) or other neurological diseases (OND). In the comparison of these two disease groups using SAM, many of the lipids exhibiting statistically higher reactivity among the MS cohort are glycerophosphocholine derivatives (q=false discovery rate) (most MS patients exhibited increased antibody reactivity these lipids as compared to reactivity in OND controls). (b) Chemical structures of the arrays lipids, exhibiting similarities to 1-palmitoyl-2-glutaroyl-sn-glycero-3-phosphocholine (PGPC). Despite structural differences in the hydrophobic regions of these lipids, these related lipids are targeted by autoantibodies in RRMS patients suggesting that these autoantibodies may target the shared polar phosphocholine region.

Identification of additional potential tolerizing (therapeutic) lipids for the treatment of MS. Based on the structure of PGPC (FIG. 7), we tested additional PGPC-related lipids to determine if anti-lipid antibody was present in CSF derived from human MS patients (FIG. 8). We found that multiple PGPC-related glycerophosphocholine lipids were targeted (at statistically increased levels) by the autoantibody response in RR MS as compared to that in OND samples (FIG. 8). Comparisons of the structures of the these lipids was performed to identify commonalities between 1-palmitoyl-2-glutaroyl-sn-glycero-3-phosphocholine (PGPC) and the other reactive lipids targeted by autoantibodies in RR MS. Despite structural differences in the hydrophobic regions of these lipids, the targeted lipids shared a polar phosphocholine region that likely represents a target of the autoantibody response in MS. Nevertheless, the side chains (non phosphocoline components) could have other functions or impacts on the capacity of these lipids to induce immune tolerance and thereby provide efficacy in MS. As described above, these PGPC-related lipids (FIG. 8) will be screened for: (i) efficacy in preventing and treating EAE (as demonstrated in FIG. 4), (ii) ability to inhibit autoreactive T (and B) cell responses as assessed by activation markers (FIG. 5a) and proliferation (FIG. 5b, 6), and (iii) pro-inflammatory cytokine production (FIG. 5b). Candidate lipids that prevent or treat EAE, reduce activation markers and T cell proliferation, and reduce proinflammatory cytokine production (and increase protective cytokine production) are likely to provide benefit in human MS.

Figure 9:
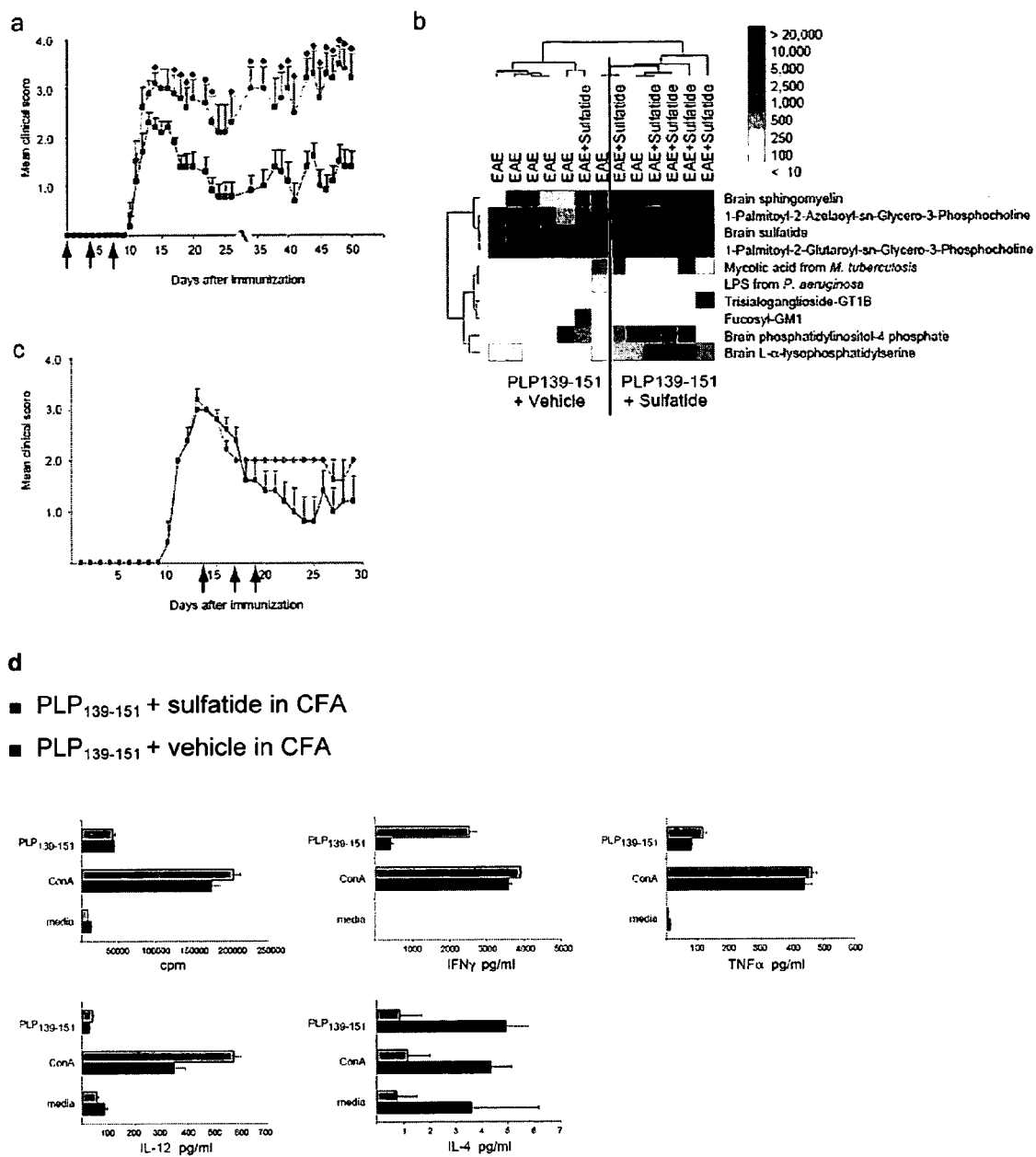
FIG. 9. Co-immunization with sulfatide plus myelin peptide results in a more severe EAE disease course. (a) Co-immunization of SJL mice with sulfatide (6 μg/mouse) and PLP$_{139-151}$ (100 μg/mouse) emulsified in CFA (■ sulfatide n=10, ■ vehicle control n=10). An additional immunization of sulfatide (6 μg/mouse) or vehicle was given i.p. on d4 and d7 post-immunization. Each point represents the mean+s.e.m. (*p<0.05; Student's t test). (b) Lipid array analysis demonstrates increased anti-lipid antibodies in serum samples derived from SJL mice co-immunized with PLP$_{139-151}$ plus sulfatide to develop EAE. The heatmap and dendrograms represent the SAM and hierarchical cluster analysis of lipid array results. (c) Modulation of EAE disease course after i.v. injection of O4 anti-sulfatide antibody versus IgM isotype control (■ O4 n=5, ■ IgM control n=5). Antibody was given on days 14, 17, and 19 post-immunization. Mice that received O4 antibody had a worse cumulative disease course compared to IgM controls following the final antibody injection (p=0.036; Student's t test). (d) Lymphocytes derived from sulfatide-treated mice (immunize with sulfatide+PLP139-151) produce increased levels of pro-inflammatory cytokines including IFNgamma and IL-12, and lower levels of Th2-type cytokines including IL-4.

Demonstration that sulfatide is a pathogenic lipid. Mice co-immunized with $PLP_{139\text{-}151}$+sulfatide exhibited a more severe disease course (FIG. 9a), and this was associated with increased anti-sulfatide and other anti-lipid antibody reactivities (FIG. 9b). Further, transfer of anti-sulfatide antibody exacerbated EAE (FIG. 9c). The encephalitogenic $PLP_{139\text{-}151}$-specific T cells from mice immunized with $PLP_{139\text{-}151}$+sulfatide produced increased amounts of the pro-inflammatory Th1 cytokines TNFα (p=0.05) and IFNγ (p=0.0007) and less of the protective Th2 cytokine IL-4 (p=0.026) in response to $PLP_{139\text{-}151}$ (FIG. 9d). Based on these data, we believe that immunization of mice with $PLP_{139\text{-}151}$+sulfatide resulted in an increase in the pathogenicity of the $PLP_{139\text{-}151}$ reactive T cells. Further, the exacerbation of mouse EAE was associated with increased lymphocyte production of pro-inflammatory cytokines. Thus, characterization of the effects of candidate lipids in the mouse EAE model for MS (EAE), both with regard to their effects on disease severity as well as the production of pro-inflammatory cytokines by autoreactive lymphocytes can be used to identify lipids likely to exacerbated MS.

Thus, we describe a "functional lipidomics" approach to discover autoimmune targets in, gain insights into pathogenic mechanisms underlying, and develop novel therapeutic approaches for multiple sclerosis. We applied lipid microarrays to identify bona fide targets of the adaptive immune response in human MS patients. We then utilized the EAE model to explore the role of these microarray-identified lipids in the pathogenesis of autoimmune demyelination, and unexpectedly discovered that one of these lipid targets, PGPC and sphingomyelin, provide efficacy in murine MS (EAE). We further demonstrated that PGPC reduces antigen-specific T cell proliferation, a mechanism by which it could attenuate pathogenic anti-myelin T cell responses to maintain tolerance. Antibodies to PGPC in individuals with multiple sclerosis could antagonize the anergy-inducing effects of PGPC, and thereby exacerbate the autoimmune state. Further studies are needed to investigate whether PGPC plays an immunoregulatory role and could provide therapeutic benefit in individuals with multiple sclerosis.

The use of the lipid autoantibody array for drug discovery is an unusual opportunity. The immune system in autoimmune disease may target molecules that have important roles in the pathobiology of the condition in question. Choosing the target of the antibody as a potential therapeutic, in this case the lipids identified on an autoantibody array, provides a fresh strategy for screening putative therapeutics. In this case, stringent statistical analysis of multiplex array data allowed selection of candidates, which then showed efficacy at two levels, disease prevention and disease reversal, in a widely used animal model, EAE, to assess potential efficacy in vivo. We have thus demonstrated that lipid array enable identification of lipids targeted by autoantibodies, affording the opportunity to mine small lipid soluble molecules as potential new drugs to treat autoimmune disease. Testing these lipids in one or more of the described assay systems (EAE model for MS; autoreactive T cell proliferation, activation marker expression, proinflammatory (IFNgamma, IL-12, IL-23) and anti-inflammatory (IL-4, IL-10) cytokine production, T cell proliferation, anergy assays; as well as analogous assays on human peripheral blood cells) can predict if the array-identified lipids act to promote inflammation (Th1 cytokines, worse EAE [sulfatide]) or promote tolerance (decreased Th1 cytokines, decreased activation markers, induction of T cell anergy [PGPC and sphingomyelin]).

It is apparent from the above results and discussion that the subject invention provides protocols for profiling lipid reactivity in autoimmune diseases, and for methods of identifying therapeutic lipids for treatment. Accordingly, the subject invention is capable of profiling a patient, and using the information thus obtained to guide treatment. As such, the subject invention represents a significant contribution to the art.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Methods

EAE induction and lipid co-immunization. For induction of EAE in C57BL/6 mice (Jackson Mice), 8-10 week old female mice were induced by subcutaneous immunization with 100 μg of $MOG_{35-55}$ emulsified in complete Freund's adjuvant (CFA; Difco Laboratories), accompanied by 300 ng of pertussis toxin (Life Technologies) intraperitoneally on days 0 and 2. For induction of EAE in SJL mice (Jackson Mice), 8- to 10-wk-old female animals were immunized subcutaneously with 100 μg of $PLP_{139-151}$ emulsified in CFA. Three injections of sulfatide (6 μg/mouse/injection) or vehicle (0.025% Tween-20 in PBS) were delivered on days 0, 4, and 7 after immunization with CNS antigens. On day 0 the sulfatide or vehicle was emulsified together with $PLP_{139-151}$ in CFA and administered by subcutaneous injection. For subsequent time points, sulfatide or vehicle was injected by the intraperitoneal route as previously described (Singh et al. (2001) *J Exp Med* 194, 1801-11). Clinical disease was monitored daily using the following scoring system: 0, no disease; 1, limp tail; 2, hindlimb weakness; 3, hindlimb paralysis; 4, hindlimb and forelimb paralysis; 5, death. Animal experiments were approved by and performed in compliance with the guidelines of the Institutional Animal Care and Use Committee.

Proliferation and cytokine assays. We sacrificed mice and harvested their lymph node cells and splenocytes. $2.5 \times 10^6$ cells/ml were stimulated in vitro with 10 μg/ml $PLP_{139-151}$, 1 μg/ml ConA, or media alone. Cells were cultured in RPMI 1640 with 10% fetal bovine serum, supplemented with L-glutamine (2 mM), sodium pyruvate (1 mM), non-essential amino acids (0.1 mM), penicillin (100 U/ml), streptomycin (0.1 mg/ml), and 2-mercaptoethanol (50 μM). To assess proliferation, 1 μCi of $^3$H-thymidine was added to each well at 48 hours for the final 18 hours of culture, and radioactivity incorporation quantified using a Betaplate scintillation counter. Cytokine assays were performed on culture supernatants after 66 hours of culture using the BD OptEIA™ Mouse IFNγ ELISA kit (BD Biosciences). Results are shown as mean of triplicates+s.e.m.

CFSE assays. LN cells were harvested from SJL/J or mice possessing a transgene encoding a T cell receptor specific for $MBP_{Ac1-11}$[29]. Cells were plated in 24-well plates at $2.5-5 \times 10^6$ cells/ml and stimulated with 1 μg/ml ConA or 5 μg/ml $MBP_{Ac1-11}$ along with 75 μM sphingomyelin and/or PGPC. Cells were stained as indicated below. 100,000 cells were collected per group per time point for each assay.

Flow cytometric analysis. Cells were stained and run on a FACScan flow cytometer (BD Biosciences) using CellQuest software (BD Immunocytometry Systems). Results were analyzed using FlowJo software version 6.3.2 (Tree Star, Inc.). The following antibody conjugates were used: PE anti-mouse CD3, clone 145-2C11; FITC anti-mouse CD4, clone GK1.5; PE anti-mouse CD4, clone GK1.5; FITC anti-mouse CD8, clone 53-6.7; PE-anti-mouse CD69, clone H1.2F3. All anti-CD3, CD4, and CD8 antibodies were purchased from BD Pharmingen. Anti-mouse CD69 was purchased from eBioscience. 7AAD staining was performed using the reagents from the Annexin V-PE Apoptosis Detection Kit I (BD Pharmingen) using the manufacturer's recommended staining protocol. CFSE staining was performed on freshly isolated lymph node cells by mixing equal volumes of 37° C. pre-warmed cells in PBS containing 5% FBS with 10 μM solution of pre-warmed CFSE probe (CellTrace™ CFSE Cell Proliferation Kit) as described in the manufacturer's alternate method for labelling cells in solution (Molecular Probes).

The invention claimed is:

1. A method for treating multiple sclerosis in a mammalian subject suffering from multiple sclerosis, the method comprising:
administering to said subject a tolerizing dose of 1-palmitoyl-2-glutaroyl-sn -glycero-3-phosphocholine (PGPC), wherein the dose of PGPC is effective to reduce the severity of the multiple sclerosis.

2. The method according to claim 1, wherein said lipid is administered in conjunction with a tolerizing adjuvant.

3. A method for treating multiple sclerosis in a mammalian subject suffering from multiple sclerosis, the method comprising:
administering to said subject a tolerizing dose of a lipid selected from 1-palmitoyl-2-glutaroyl-sn-glycero-3-phosphocholine (PGPC); 1-palmitoyl-2-(9'oxo-nonanoyl)-sn-glycero-3-phosphocholine; 1-palmitoyl-2-arachinodoyl-sn-glycero-3-phosphocholine;

1-palmitoyl-2-myristoyl-sn-glycero-3-phosphocholine; 1-palmitoyl-2-hexadecyl-sn-glycero-3-phosphocholine; 1-palmitoyl-2-azelaoyl-sn-glycero-3-phosphocholine; and 1-palmitoyl-2-acetoyl-sn-glycero-3-phosphocholine wherein the dose is effective to reduce the severity of the multiple sclerosis.

4. A method for treating multiple sclerosis in a mammalian subject suffering from multiple sclerosis, the method comprising:

administering to said subject a tolerizing dose of a lipid having the structure:

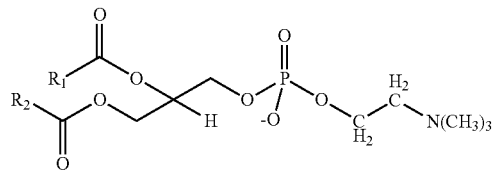

where $R_1$ is $(CH_2)_n CO_2 H$ where n is from 1 to 10; and $R_2$ is palmitoyl;

wherein the dose is effective to reduce the severity of the multiple sclerosis.

5. The method according to claim 4, wherein said lipid is selected from 1-palmitoyl-2-glutaroyl-sn-glycero-3-phosphocholine (PGPC); 1-palmitoyl-2-(9'-oxo-nonanoyl)-sn-glycero-3-phosphocholine.

* * * * *